(12) United States Patent
Kahlon et al.

(10) Patent No.: US 12,102,478 B2
(45) Date of Patent: Oct. 1, 2024

(54) USER-ATTACHABLE/DETACHABLE IMAGING CATHETER

(71) Applicant: IVUSLIDE, Inc., Wilmington, DE (US)

(72) Inventors: Arunpreet Kahlon, Highlands Ranch, CO (US); Tim A. Fischell, Kalamazoo, MI (US)

(73) Assignee: IVUSLIDE, Inc., Wilmington, DE (US)

( * ) Notice: Subject to any disclaimer, the term of this patent is extended or adjusted under 35 U.S.C. 154(b) by 0 days.

(21) Appl. No.: 18/309,183

(22) Filed: Apr. 28, 2023

(65) Prior Publication Data

US 2024/0215946 A1    Jul. 4, 2024

Related U.S. Application Data

(60) Provisional application No. 63/478,432, filed on Jan. 4, 2023.

(51) Int. Cl.
*A61B 8/12*      (2006.01)
*A61B 5/00*      (2006.01)
(Continued)

(52) U.S. Cl.
CPC .............. *A61B 8/12* (2013.01); *A61B 5/0084* (2013.01); *A61B 8/4263* (2013.01);
(Continued)

(58) Field of Classification Search
CPC ....... A61B 8/12; A61B 8/4263; A61B 8/4422; A61B 5/0084; A61B 2562/247; A61B 2090/3782; A61B 2090/3784; A61F 2/958
See application file for complete search history.

(56) References Cited

U.S. PATENT DOCUMENTS 6,780,199 B2    8/2004  Solar et al.
7,651,521 B2    1/2010  Ton et al.
(Continued)

FOREIGN PATENT DOCUMENTS

WO    WO-9934749 A1     7/1999
WO    WO-2021058286 A1  4/2021
WO    WO-2023039511 A1  3/2023

OTHER PUBLICATIONS

U.S. Appl. No. 17/472,450 U.S. Pat. No. 11,510,798, filed Sep. 10, 2021, Intravascular Ultrasound (IVUS) Ostial Stent Delivery System and Method.
(Continued)

*Primary Examiner* — Sarah A Long
(74) *Attorney, Agent, or Firm* — Schwegman Lundberg & Woessner, P.A.

(57) ABSTRACT

An imaging catheter apparatus can include an elongate shaft assembly having a proximal shaft portion and a distal shaft portion. The shaft assembly can be configured to carry an imaging transducer such that the imaging transducer is locatable at or near a distal portion of the elongate shaft assembly. At least one coupler can be attached to the elongate shaft assembly. The at least one coupler configured to permit an end user to at least one of couple or attach at least one of a guidewire or an interventional medical device to the elongate shaft assembly via the at least one coupler. For example, the at least one coupler can include an elastic sleeve. The elastic sleeve can expand to accommodate passage of a guidewire or interventional medical device therethrough. Then, the elastic sleeve can relax or shrink to grip the interventional medical device, such as to secure or stabilize its position with respect to the imaging catheter, such as for performing a medical procedure.

20 Claims, 15 Drawing Sheets

(51) Int. Cl.
*A61B 8/00* (2006.01)
*A61F 2/958* (2013.01)
(52) U.S. Cl.
CPC ............ *A61B 8/4422* (2013.01); *A61F 2/958* (2013.01); *A61B 2562/225* (2013.01); *A61B 2562/247* (2013.01)

(56) References Cited

U.S. PATENT DOCUMENTS

| | | | |
|---|---|---|---|
| 10,117,564 B2* | 11/2018 | Frankel | A61B 8/06 |
| 11,510,798 B1 | 11/2022 | Kahlon | |
| 2005/0136385 A1* | 6/2005 | Mann | A61N 1/025 434/320 |
| 2007/0249939 A1* | 10/2007 | Gerbi | A61B 18/1477 600/462 |
| 2009/0182281 A1 | 7/2009 | Kurth et al. | |
| 2012/0108979 A1 | 5/2012 | Franklin et al. | |
| 2013/0023802 A1 | 1/2013 | Mcintosh et al. | |
| 2014/0128726 A1 | 5/2014 | Quill et al. | |
| 2014/0276028 A1 | 9/2014 | Stigall et al. | |
| 2015/0265816 A1 | 9/2015 | Campbell | |
| 2019/0350648 A1* | 11/2019 | Owens | A61B 1/00071 |
| 2020/0129196 A1* | 4/2020 | McCaffrey | A61B 17/22022 |
| 2020/0360164 A1 | 11/2020 | Janku et al. | |
| 2021/0259860 A1 | 8/2021 | Walzman | |

OTHER PUBLICATIONS

"U.S. Appl. No. 17/472,450, Advisory Action Before the Filing of an Appeal Brief mailed Aug. 11, 2022", 5 pgs.

"U.S. Appl. No. 17/472,450, Examiner Interview Summary mailed Apr. 18, 2022", 2 pgs.

"U.S. Appl. No. 17/472,450, Final Office Action mailed May 20, 2022", 57 pgs.

"U.S. Appl. No. 17/472,450, Non Final Office Action mailed Feb. 2, 2022".

"U.S. Appl. No. 17/472,450, Notice of Allowance mailed Sep. 14, 2022", 8 pgs.

"U.S. Appl. No. 17/472,450, Response filed Apr. 18, 2202 to Non Final Office Action mailed Feb. 2, 2022", 15 pgs.

"U.S. Appl. No. 17/472,450, Response filed Jul. 19, 2022 to Final Office Action mailed May 20, 2022".

"U.S. Appl. No. 17/472,450, Response filed Aug. 15, 2022 to Advisory Action mailed Aug. 11, 2022", 14 pgs.

"International Application Serial No. PCT/US2022/076181, International Search Report mailed Dec. 29, 2022", 4 pgs.

"International Application Serial No. PCT/US2022/076181, Written Opinion mailed Dec. 29, 2022", 4 pgs.

Lichaa, Hady, et al., "Coronary stent positioning under live IVUS guidance in low contrast percutaneous coronary interventions: The live IVUS stenting technique". Wiley, Catheter Cardiovasc Interv. 2021;1-8., (2021), 9 pgs.

* cited by examiner

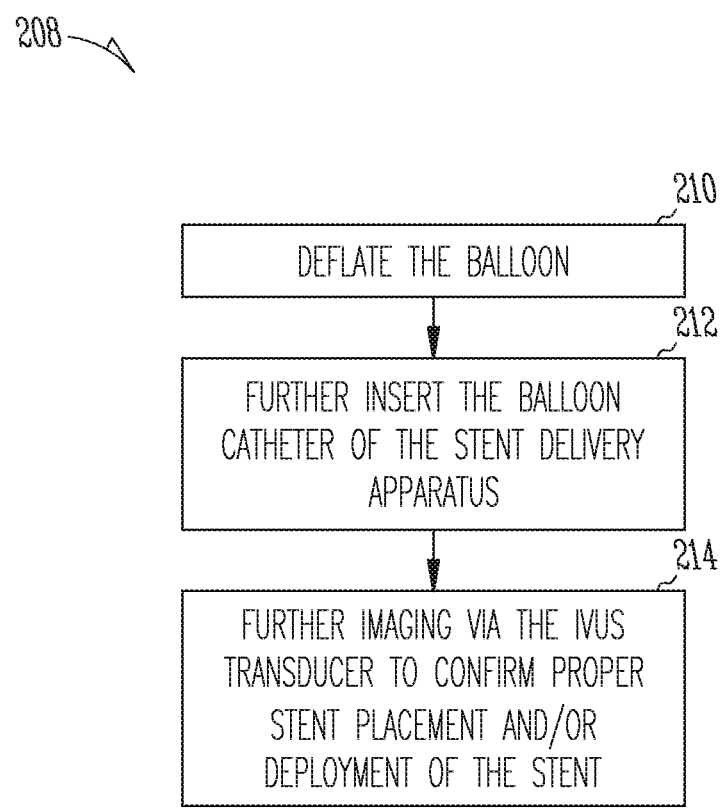

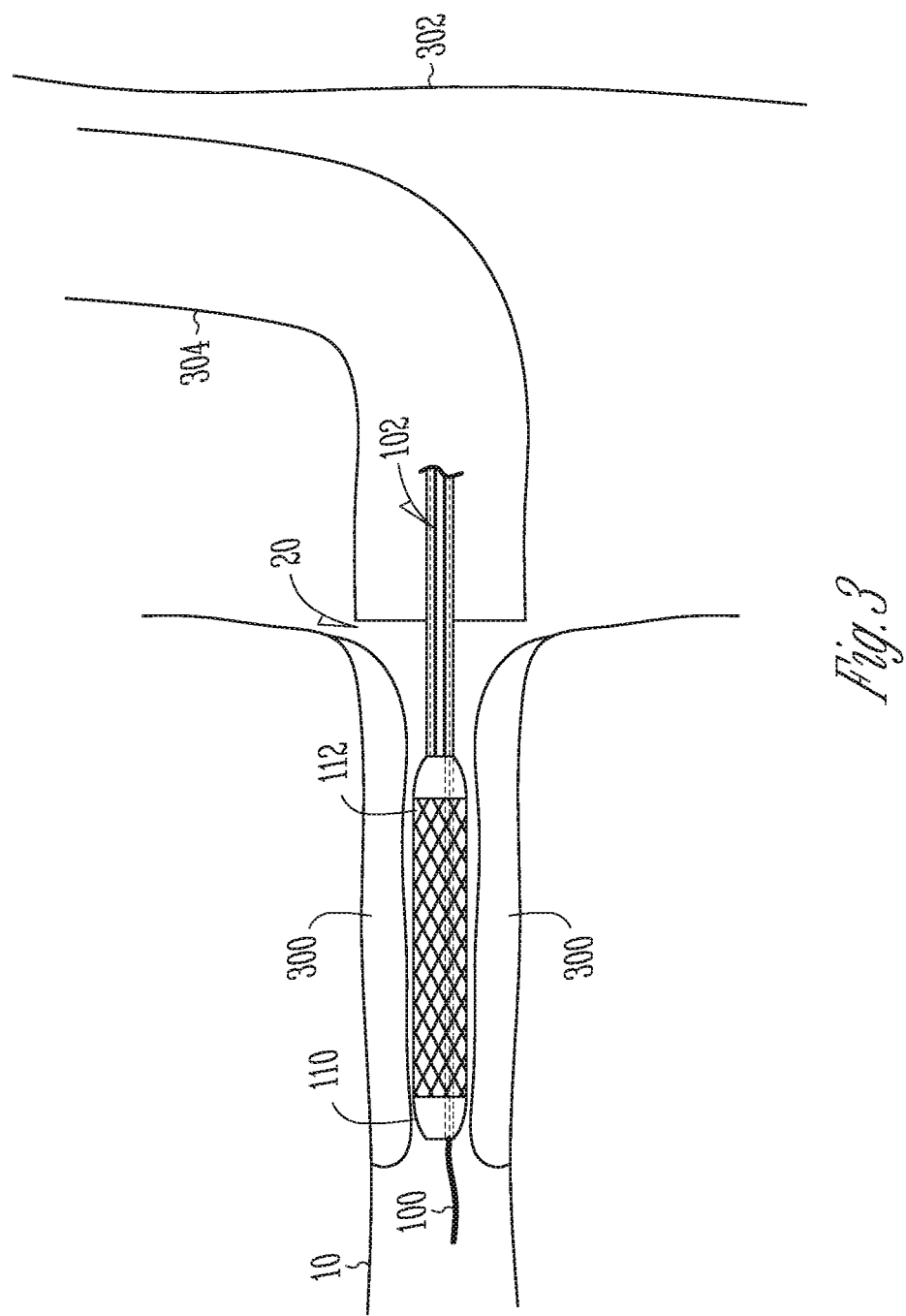

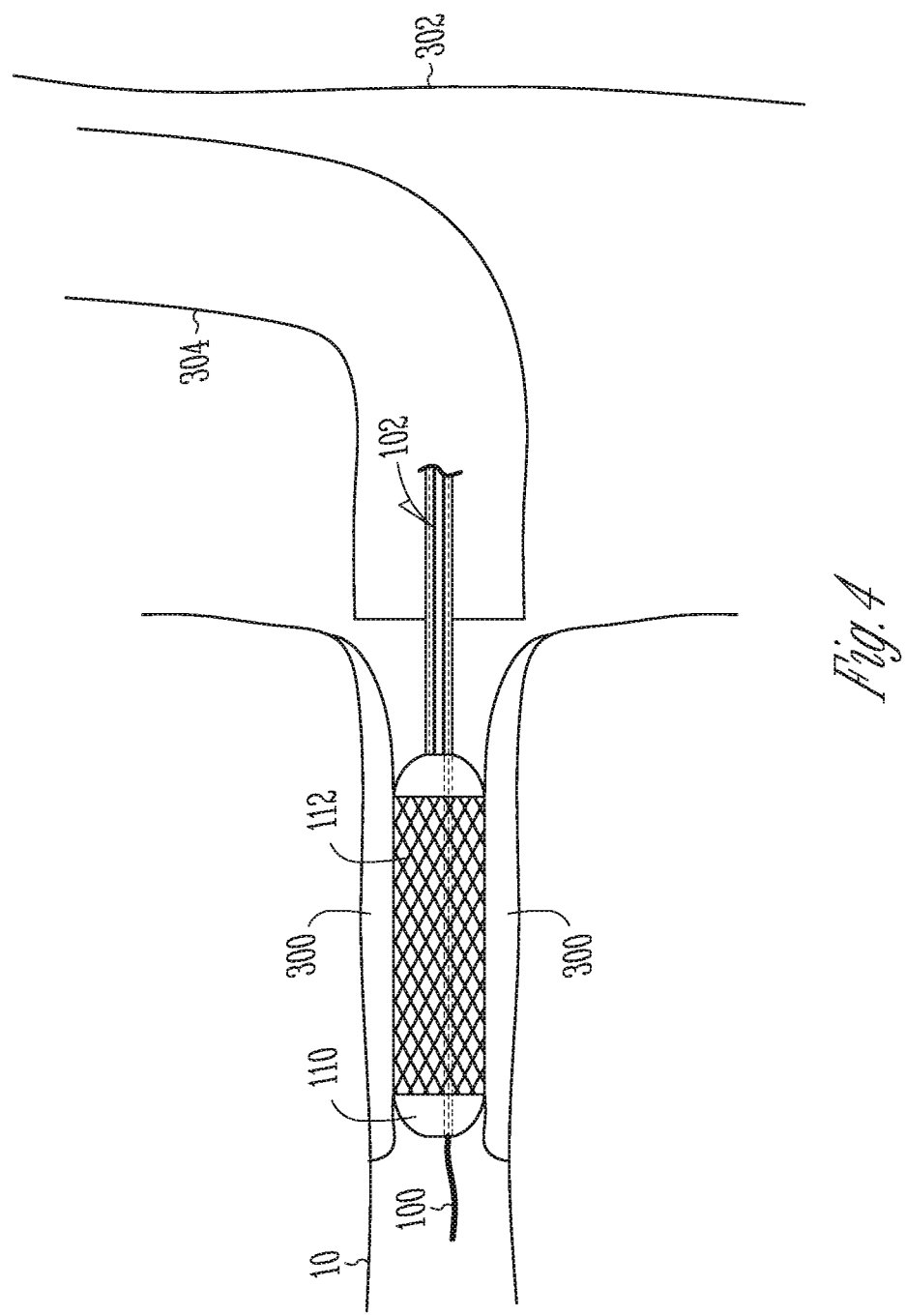

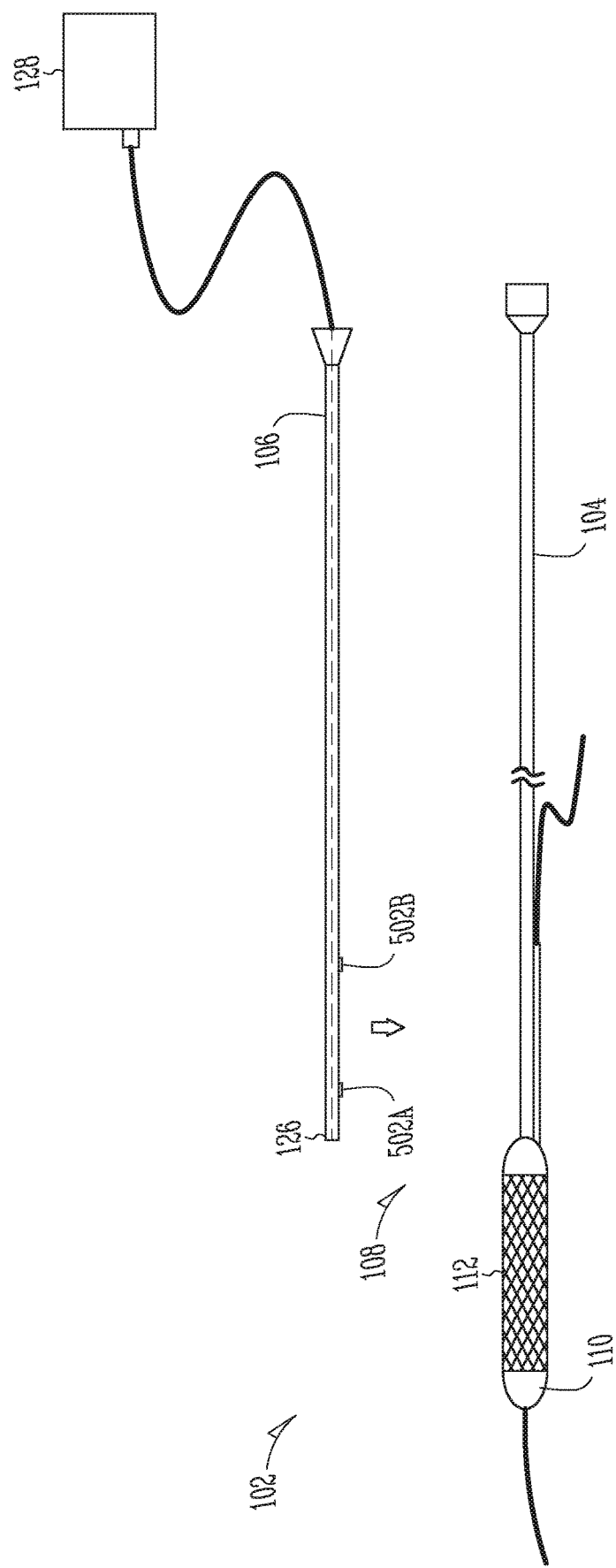

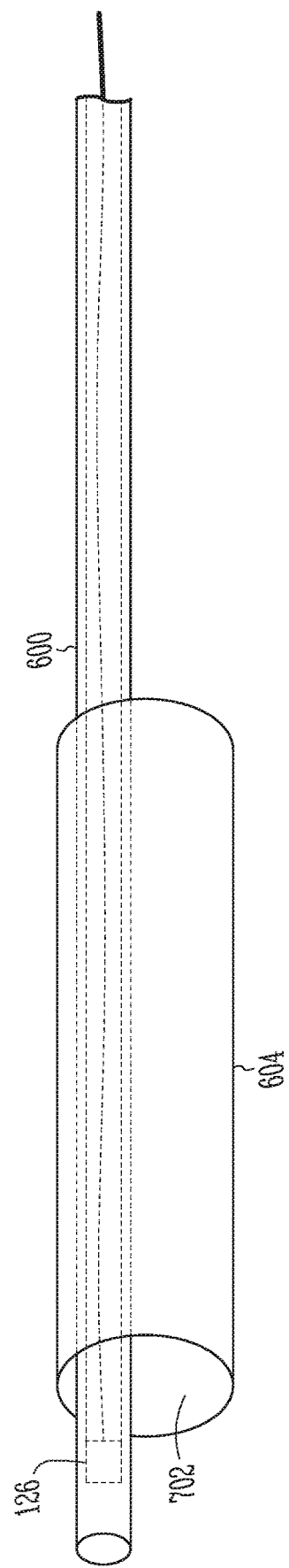

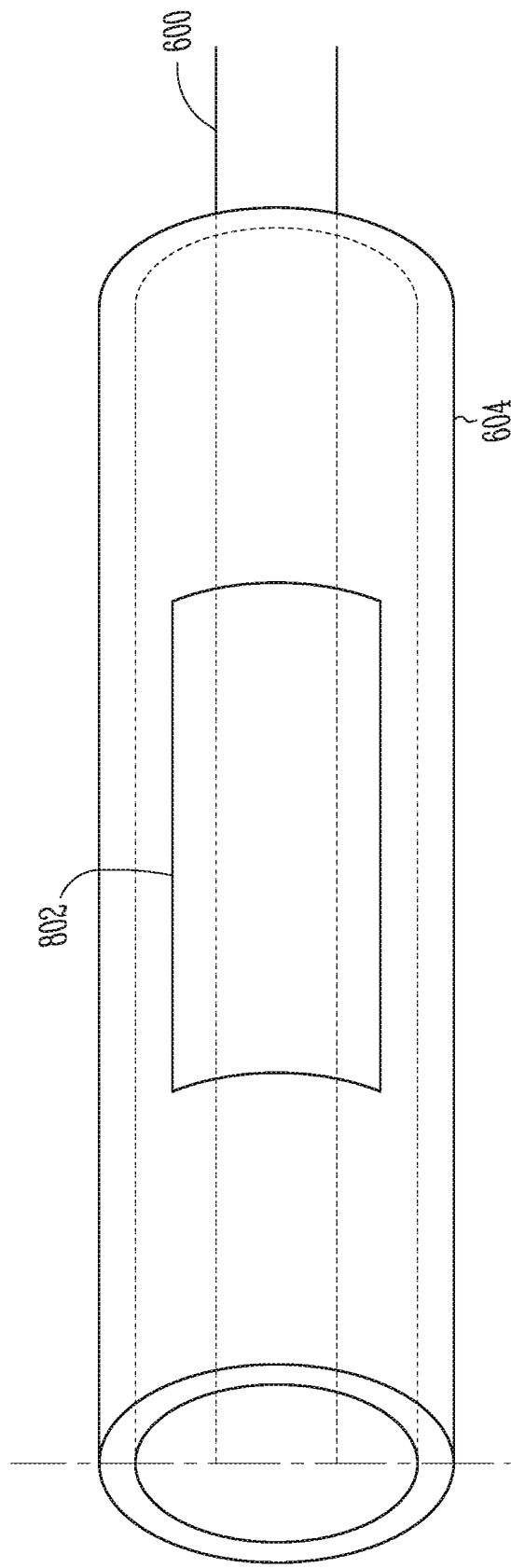

USER-ATTACHABLE/DETACHABLE IMAGING CATHETER

CLAIM OF PRIORITY

This U.S. Patent Application claims the benefit of priority of Arunpreet Kahlon, U.S. Provisional Patent Application No. 63/478,432, filed Jan. 4, 2023, entitled OSTIAL STENT DELIVERY WITH USER-ATTACHABLE/DETACHABLE INTRAVASCULAR ULTRASOUND (IVUS).

CROSS REFERENCE TO RELATED PATENT DOCUMENTS, AND INCORPORATION BY REFERENCE

This U.S. patent application incorporates by reference: (1) Arunpreet Kahlon, PCT Patent Application No. PCT/US2022/076181, filed on Sep. 9, 2022, entitled INTRAVASCULAR ULTRASOUND (IVUS) OSTIAL STENT DELIVERY SYSTEM AND METHOD; (2) Arunpreet Kahlon, U.S. patent application Ser. No. 17/472,450, filed on Sep. 10, 2021, entitled INTRAVASCULAR ULTRASOUND (IVUS) OSTIAL STENT DELIVERY SYSTEM AND METHOD, which issued on Nov. 29, 2022 as U.S. Pat. No. 11,510,798; and (3) Arunpreet Kahlon, U.S. Provisional Patent Application No. 63/478,432, filed Jan. 4, 2023, entitled OSTIAL STENT DELIVERY WITH USER-ATTACHABLE/DETACHABLE INTRAVASCULAR ULTRASOUND (IVUS).

TECHNICAL FIELD

This document relates generally to vascular intervention, interventional cardiology, radiology, vascular surgery, and particularly, but not by way of limitation to an imaging catheter that is end-user-attachable to and end-user-detachable from an interventional catheter or other interventional device to be used with the imaging catheter.

BACKGROUND

A stent is a type of an endoprosthesis device. A stent may be placed or implanted within a vein, artery, or other tubular body organ or vessel, such as for treating occlusions, stenoses, or aneurysms of a vessel by reinforcing the wall of the vessel or by expanding the vessel. A stent is generally a longitudinal tubular device of biocompatible material, for example, stainless steel, cobalt-chromium, nitinol, or a biodegradable material, providing a flexible scaffold framework of struts that can be radially expanded, such as by using a balloon catheter, or self-expanded within the vessel, such as by using a shape memory characteristic of the material. The struts are configured to move and thereby to allow the stent to be compressed or "crimped" into a smaller outer diameter so that they can be mounted inside a stent delivery system such as for delivery to, and expandable deployment at, a desired intravascular location.

While only a relatively small percentage of stents are deployed at an ostium, ostial stenting is a particularly important and challenging location for deploying a stent. An ostium refers to the mouth of the blood vessel, at which it joins another vascular structure. For example, a coronary artery can exit the aorta just above the aortic valve at a coronary ostium. Similarly, a renal artery may exit the aorta at an ostium. While attempting to deploy a stent accurately at an ostium of a vessel, it may be very difficult to position the stent at the true ostium of the vessel. For example, stenting a lesion located at such a coronary ostium involves properly placing and deploying the stent in a manner that spans the coronary ostium—not too deep into the coronary vessel such that the ostium is not supported by the expanded stent—but also in a manner such that the stent does not protrude from the coronary ostium out into the aorta. A protruding stent can cause blood flow turbulence, and can impede any later intervascular stenting procedure, such as at a location along the aorta that is located beyond any such protruding stent.

Proper stent placement at an ostium is difficult to verify fluoroscopically or angiographically. For example, directionality of such ostial structures is difficult to ascertain from an angiographic 2-dimensional (2D) projection of a 3-dimensional (3D) blood vessel structure. In 3D, the blood vessel structure can exhibit bends and turns in all 3 dimensions. Depending on the angle from which the X-ray fluoroscopy image is obtained, the blood vessel can appear shortened. Any misrepresentation of the ostium on the X-ray projection used in fluoroscopic imaging can therefore lead to the possibility of mispositioning the stent with respect to the desired ostium location.

Intravascular Ultrasound (IVUS) imaging can be used for imaging atherosclerosis and other vessel diseases and defects. In an IVUS imaging procedure, an IVUS catheter is threaded over a guidewire into a blood vessel of interest. IVUS images are acquired of the atherosclerotic plaque and surrounding area. Existing IVUS imaging techniques, however, generally involve removing the IVUS imaging catheter from the guidewire, then inserting a stent delivery apparatus over the guidewire to deliver and deploy the stent at a desired location. After stent delivery and deployment, the stent delivery apparatus is removed. Then, the IVUS imaging catheter is re-inserted for further imaging to confirm proper stent deployment.

SUMMARY

The present inventors have recognized, among other things, that existing IVUS techniques are time-consuming and inconvenient. In particular, existing IVUS techniques are not well-suited for the less common but particularly challenging task of placing and deploying an ostial stent. Even if the interventional cardiologist were to exchange the stent delivery apparatus for an IVUS imaging catheter, to confirm proper stent placement and deployment, the present inventors have recognized that it would be far more advantageous to have a convenient and usable system for employing IVUS to determine proper stent location before deploying the stent, so that the stent can actually be properly deployed at the desired location with respect to the ostium.

One approach to using intravascular imaging for assisting in stent placement and employment might be to insert into a guide catheter: (1) a separate IVUS imaging catheter (e.g., over a first guidewire) and (2) a separate balloon catheter stent delivery device (e.g., over a second guidewire). However, an approach using a separate IVUS imaging catheter and a separate stent delivery device is bulky and may be unusable in a stenosed blood vessel or ostium to be treated.

For example, the present document and U.S. Pat. No. 11,510,798 describes an integrated (unitary) intravascular ultrasound (IVUS) imaging transducer that can be carried onboard and combined with an ostial stent delivery apparatus, such as which can be used in a method of deploying a stent at a blood vessel ostium. First, a balloon carrying a stent can be inserted into a coronary blood vessel ostium using a balloon catheter of the stent delivery apparatus.

Second, the ostium can be intravascularly imaged, such as from an imaging transducer that is located with the stent delivery apparatus, such as at a location that is at least in part proximal to the balloon carrying the stent. This imaging can be used to determine a stent location with respect to the ostium. Third, when the imaging indicates that the stent is at the desired stent location with respect to the ostium, then the balloon can be expanded to expandably deploy the stent at the desired stent location.

This method can include inserting an intravascular ultrasound (IVUS) transducer—as part of an integrated unitary stent delivery apparatus that also includes the balloon, sharing a common elongate shaft, such that both the IVUS transducer and the balloon can be introduced into the vasculature, via a guidewire, as a single unitary instrument. For example, the transducer can be inserted in a fixed arrangement with respect to the balloon.

Alternatively (or additionally), this method can include inserting a removable intravascular ultrasound (IVUS) transducer to a desired location with respect to the balloon via an IVUS lumen that is in a fixed arrangement with respect to the balloon. Optionally, the method can further include removing the ultrasound transducer by extracting the ultrasound transducer via the IVUS lumen to an external location. Optionally, the removable ultrasound transducer can be at least one of reprocessed or resterilized, such as for allowing re-use of the ultrasound transducer for a subsequent procedure.

Optionally, the method can further include: deflating the balloon; further inserting (or alternatively slightly retracting) the balloon catheter of the stent delivery apparatus; and further imaging via the transducer to confirm stent deployment and desired apposition with respect to the vascular structure of the blood vessel, the ostium, or both.

The method can include inserting a portion of the balloon catheter using one or both of a monorail/rapid-exchange or an over-the-wire technique.

In an example, the integrated intravascular ultrasound (IVUS) ostial stent delivery apparatus can include a balloon catheter. The balloon catheter can include an elongate shaft having a proximal shaft portion and a distal shaft portion and defining (1) a longitudinal inflation lumen and (2) a longitudinal IVUS lumen extending between the proximal shaft portion and the distal shaft portion. A balloon can be located at and about the distal shaft portion and in fluid communication with the inflation lumen. The shaft further defines a longitudinal guidewire lumen, extending at least through the distal shaft portion underlaying the balloon for at least a length of the balloon along the shaft. An IVUS ultrasound imaging transducer is at least one of locatable at or affixed to the distal shaft portion and located at least in part proximally to the balloon to permit imaging of a coronary blood vessel ostium including before expandably deploying a stent at or near the ostium by inflating the balloon. The balloon catheter can also include a transduced IVUS signal conduit coupled to the transducer and passing through the IVUS lumen to the proximal shaft portion for coupling to and signal processing by patient-external processing circuitry couplable thereto.

In an example, the integrated intravascular ultrasound (IVUS) ostial stent delivery apparatus can include a balloon catheter. The balloon catheter can include an elongate shaft having a proximal shaft portion and a distal shaft portion and defining (1) a longitudinal inflation lumen and (2) a longitudinal IVUS lumen extending between the proximal shaft portion and the distal shaft portion. A balloon can be located at and about the distal shaft portion and in fluid communication with the inflation lumen. The shaft further defines a longitudinal guidewire lumen, extending at least through the distal shaft portion underlaying the balloon for at least a length of the balloon along the shaft. The IVUS lumen is sized and shaped and arranged to pass an IVUS ultrasound imaging transducer to a location at or just proximal to the balloon to permit imaging of a coronary blood vessel ostium including before expandably deploying a stent at or near the ostium by inflating the balloon.

The present document describes techniques that can allow real-time image-guidance any of before, during, and after stent delivery and deployment, such as can be particularly useful in the challenging case of properly placing and deploying a stent at a coronary ostium. This can help avoid problems with sub-optimal ostial stent placement or deployment, such as explained herein.

The present document further describes, among other things, examples of an IVUS, an optical coherence tomography (OCT), or other imaging catheter that is configured to permit an end-user to attach the imaging catheter to an interventional catheter or other interventional device. For example, the imaging catheter can include an elastic sleeve, such as at a distal portion of the imaging catheter. An interventional catheter or other interventional device can be inserted through the sleeve by a physician or other end-user, such as to attach the imaging catheter to a balloon catheter for stent delivery or to another interventional device for another purpose.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 2B is a flow chart showing an example of portions of a method of using onboard imaging of a stent delivery device to confirm proper placement of the stent, after expanding and deploying the stent at the desired location using the balloon of the balloon catheter provided by the stent delivery device.

FIG. 3 shows a schematic illustration of the stent delivery device with the stent unexpanded at an ostial lesion, with the guide catheter routing the stent delivery device back through the vasculature.

FIG. 4 is similar to FIG. 3, but with the stent having been expanded by the balloon.

FIG. 5 shows an example of portions of the stent delivery device of FIG. 1B, such as which can include one or both of an end-user-attachable or an end-user-detachable inflation tube and IVUS tube.

FIG. 7 shows an example of an imaging catheter with an elastic sleeve, such as with a portion of the imaging catheter passing through and affixed within a longitudinal lumen of the elastic sleeve.

FIG. 8 shows an example of the elastic sleeve in which an open or other imaging window can be included.

DETAILED DESCRIPTION

This document describes, among other things, examples of an IVUS, an optical coherence tomography (OCT), or other imaging catheter that is configured to permit an end-user to attach the imaging catheter to an interventional catheter or other interventional medical device ("interventional device"). For example, the imaging catheter can include an elastic sleeve, such as at a distal portion of the imaging catheter. An interventional catheter or other interventional device can be inserted through the sleeve by a physician or other end-user, such as to attach the imaging catheter to a balloon catheter for stent delivery or to another interventional device for another purpose.

As an illustrative, non-limiting use case, the present techniques can be useful for IVUS image-guided stent placement at a blood vessel ostium (e.g., coronary vessel ostium, renal vessel ostium, or the like) to treat an ostial lesion. An IVUS transducer can be integrated with the stent delivery device. This can give the physician better visualization information. Such IVUS imaging information can include accurate 3-dimensional (3D) full circumferential (e.g., 360 degrees) visualization information. The IVUS imaging information can be used by the physician in real-time, such as to help avoid placing the stent sub-optimally. An example of sub-optimal ostial stent placement includes placing the stent too deep within a blood vessel lumen so as to be ineffective at treating the ostial lesion. Another example of sub-optimal ostial stent placement includes placing the stent protruding too-far out of the blood vessel ostium into source vasculature. Such a protruding stent can create blood flow turbulence and can impede subsequent stenting procedures. The present techniques can help provide better imaging information to the physician for guiding stent placement than what is available using fluoroscopy or angiography.

Figure 1A:
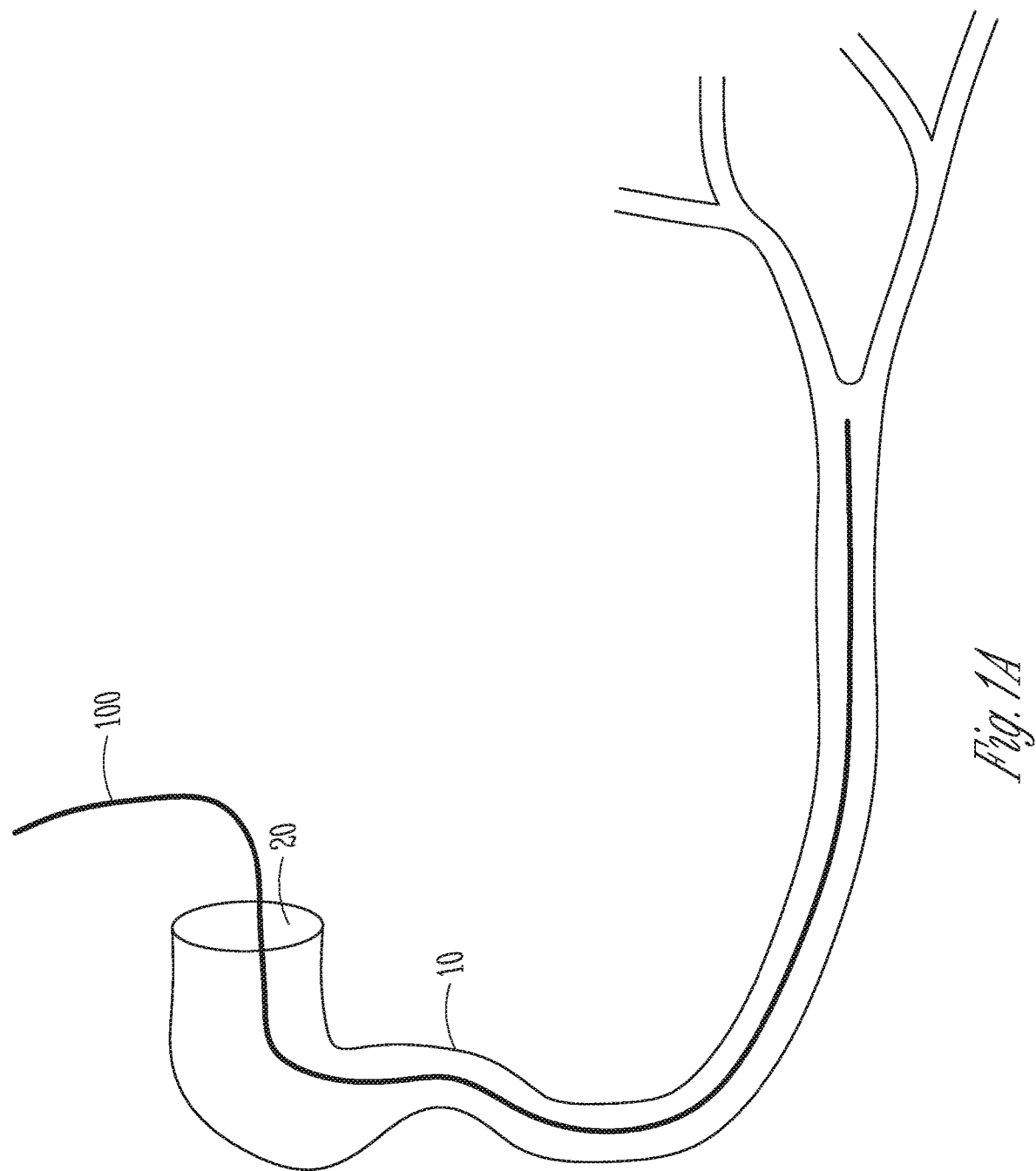
FIG. 1A is a schematic illustration of a coronary vessel with a guidewire having been introduced into the coronary vessel through the coronary ostium.

FIG. 1A is a schematic illustration of a blood vessel, such as a coronary artery 10. A guidewire 100 has been introduced, via a guide catheter (not shown), into the coronary vessel 10, through the coronary ostium 20. The ostium 20 opens into a larger vascular structure, such as the aorta. For treating an ostial lesion via a stent, it is desired to place the stent such that a proximal end of the stent either (1) aligns with the plane defined by the ostium 10 opening into the larger vascular structure of the aorta, or (2) such that the proximal end of the stent only minimally protrudes into such larger vascular structure of the aorta.

Figure 1B:
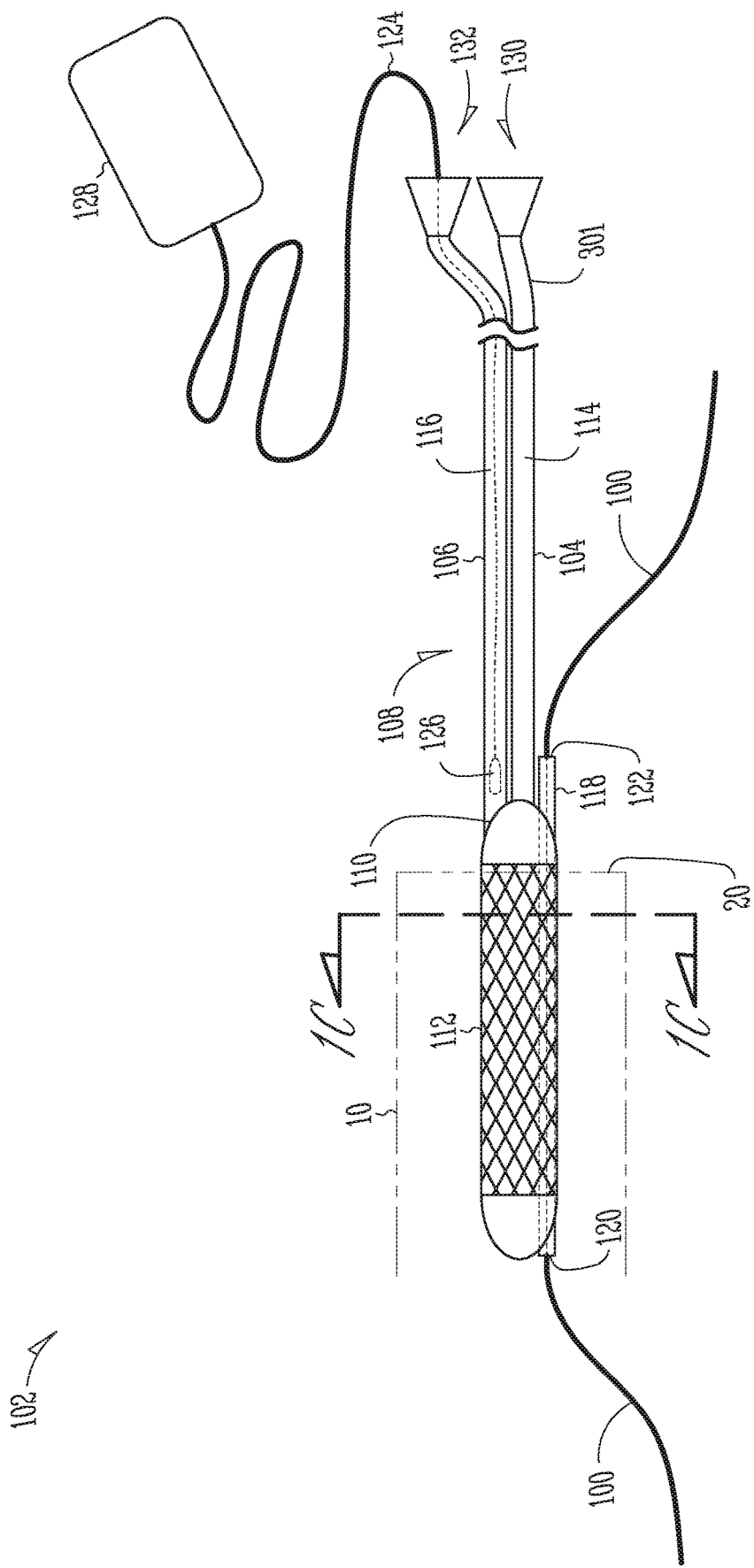
FIG. 1B is a schematic illustration showing a side view of portions of an embodiment of a guided stent delivery system that can include a stent delivery device.

FIG. 1B is a schematic illustration showing a side view of portions of an embodiment of an image-guided stent delivery system that can include a stent delivery device 102. In FIG. 1B, the stent delivery device 102 is shown with the guidewire 100 extending through the coronary vessel 10 and its ostium 20. In FIG. 1B, the stent delivery device 102 includes an integrated stent-delivery balloon catheter and IVUS catheter sharing a common elongate shaft 108. A distal portion of the elongate shaft 108 includes a balloon 110 about an outer circumference of the elongate shaft 108. The uninflated balloon 110 carries an unexpanded stent 112. In FIG. 1B, the stent 112 is shown, with respect to the ostium 20, with the proximal end of the stent 112 being aligned with the plane defined by the ostium 20 opening into the larger vascular structure of the aorta, such as is desired for good ostial stenting.

The shaft 108 can include a first hypotube or other similar tubular inflation tube 104 structure defining an inflation lumen 114. The inflation lumen 114 is arranged to provide a fluid communication conduit extending from within the balloon 110, located at the distal portion of the shaft 108, to a proximal portion of the elongate shaft 108. At or near the proximal end of the elongate shaft 108, the fluid communication conduit of the inflation lumen 114 can include a Luer coupling. The Luer coupling can provide a port for providing a further fluid communication conduit passage for coupling to a syringe or pump or other fluid inflation and deflation source that is located external to the patient. The balloon 110 can be inflated by pumping or otherwise directing a quantity of an inflation fluid (e.g., saline solution and fluoroscopic imaging contrast agent mixture) from the inflation and deflation source. The fluid is directed toward the balloon 110 via the inflation lumen 114, such as for inflating the balloon 110. Inflating the balloon 110 expands the stent 112. Expanding the stent 112 deploys the stent 112 into apposition with the vasculature, such as with a proximal end of the stent 112 aligned with the plane defined by the opening of the ostium 20 into the larger vascular structure of the aorta. The syringe or other inflation or deflation source can be used to withdraw fluid from the balloon 110 via the inflation lumen 114 to deflate the balloon 110, leaving the expanded stent 112 deployed and supporting the surrounding vascular region.

The shared elongate shaft 108 can also include a second hypotube or other similar tubular IVUS tube 106 structure defining an IVUS lumen 116. For example, the IVUS lumen 116 can extend from a proximal portion of the shaft 108 at least to a proximal edge of the balloon 110. The IVUS lumen 116 may terminate at the proximal edge of the balloon 110. Alternatively, the IVUS lumen 116 may optionally extend even further into a distal portion of the shaft 108 underlying the balloon 110. The IVUS lumen 116 can extend distally beyond the distal edge of the balloon 110, such as toward the distal tip of the elongate shaft 108. The IVUS lumen 116 can be hermetically sealed, including at its termination location at the distal portion of the elongate shaft 108 of balloon catheter 114, such as to inhibit fluid ingress into the IVUS lumen 116 from within the vasculature.

The IVUS lumen 116 can be sized, shaped, and otherwise configured to allow passage or carrying of an elongate IVUS probe 124 or catheter, such as can be either fixed within or removably inserted within the IVUS lumen 116. For example, the IVUS tube 106 can define an IVUS lumen 116 having an inner diameter of 1 mm or less. The IVUS probe 124 includes an IVUS transducer 126, such as can be located at a distal portion or distal tip of the IVUS probe. For example, the IVUS transducer 126 can include either a spinnable component to provide 360 degree circumferential imaging from various different circumferential locations, or a phase-array or scannable set of components to provide 360 degree circumferential imaging from various different circumferential locations. The IVUS transducer 126 can be located at or near a distal portion of the IVUS probe 124. For example, all or a portion of the IVUS transducer 126 can be located just proximal to the balloon 110. Alternatively, all or a portion of the IVUS transducer 126 can optionally be located or locatable under all or a portion of the balloon 110 extending about the elongate shaft 108.

The IVUS probe 124 provides an IVUS signal communication conduit for the transduced IVUS signal, back from the IVUS transducer 126 through the IVUS probe 124 and to external interface componentry 128 coupled thereto. The external interface componentry can include a pullback actuator or motor and instrumentation circuitry, which can include a microprocessor or other signal processing circuitry, such as for signal-processing the IVUS transducer signal data into a 360 degree circumferential visualization image.

The pullback actuator or motor can be used to withdraw the IVUS transducer 126 at a specified rate, while concurrently taking 360 degree circumferential images that can be stitched together to form a cylindrical 360 degree image over the longitudinal distance traversed by the IVUS transducer 126 during the mechanized withdrawal. This resulting image can be displayed on a display screen for the user, such as in real-time during stent delivery and after the stent has been delivered and deployed.

As explained further below, because the IVUS transducer 126 is located at a specified distance from an edge of the stent 112 on the stent delivery device 102, the stent delivery device 102 can be inserted into the coronary vessel 10 slightly beyond the desired ostial location of the stent 112, and the pullback actuator or motor can be used to withdraw the IVUS probe to generate the cylindrical sequence of circumferential images from the IVUS transducer 126, which imaging can show the ostial plane opening into the larger vasculature of the aorta. Then, the stent delivery device 102 can similarly be withdrawn by a similar amount (with an additional incremental amount to account for a distance between the proximal edge of the stent 112 and the IVUS transducer 126). Then the balloon 110 can be expanded to properly deploy the stent 112 at the desired location with the proximal edge of the stent 112 aligned with the plane of the ostium opening into the aorta.

The shaft 108 can also include third hypotube or other similar channel structure defining a guidewire lumen 118. The guidewire lumen 118 can extend along at least along the distal portion of the shaft 108, underlying the circumferentially surrounding balloon 110. The guidewire lumen 118 can extend from a guidewire distal exit port 120, which is distal to the balloon 110, to a guidewire proximal exit port 122. The guidewire proximal exit port 122 can be located somewhat proximal to the proximal edge of the balloon 110, such as at or near the midpoint of the stent delivery device 102. As an illustrative example, the proximal exit port 122 can be 25-30 centimeters from the distal tip of the stent delivery device 102), in a "rapid-exchange" embodiment. Thus, the proximal exit port 122 can be located somewhat proximal to a proximal edge of the balloon 110 (e.g., mid-shaft, in "rapid exchange" configuration), or can be located anywhere more proximally—even at or near the proximal end of the shaft 118 (in an "Over The Wire" or "OTW" configuration), such as illustrated in FIG. 1D.

The guidewire lumen 118 can be sized, shaped, and otherwise configured to pass the guidewire 100 through the guidewire lumen 118. But with the guidewire 100 already in place within a guide catheter within the vasculature, such as extending to or passing by the lesion location of interest, such as the ostium (20), the balloon catheter 104 can be introduced and passed along the guidewire (100). In this manner, the guidewire (100) can be used for introducing balloon catheter 104 to an appropriate location within the vasculature, such as for delivering, positioning, and deploying the unexpanded stent 112 such as under guidance of the visualization provided by the IVUS transducer 126 to the user. Optionally, in an OTW embodiment, the guidewire lumen 118 can extend substantially or completely along the entire length of the shaft 108 of the balloon catheter 104 to a proximal exit port 122 that is located at or near the proximal end of the shaft 108 of the balloon catheter 104.

In FIG. 1B, to recap and further explain, the stent delivery device 102 is shown as providing a balloon catheter and having an elongate shaft 108 with suitable flexibility and rigidity to be introduced intravascularly, such as via a guide catheter (see FIG. 3) and the guide wire 100, to position the distal balloon 110 carrying the stent 112 into a coronary ostium 20 and within the coronary vessel branching and extending inward therefrom. The elongate shaft 108 can include an elongate member or structure such as can include adjacent hypotubes (e.g., the inflation tube 104 and the IVUS tube 108) that can be affixed to each other, or co-formed together. These adjacent hypotubes can extend side-by-side longitudinally along the length of the elongate shaft 108, such as to respectively provide corresponding side-by-side longitudinal lumens: (1) the inflation lumen 114; and (2) the IVUS lumen 116. This arrangement of a side-by-side inflation lumen 114 and IVUS lumen 116 can extend from a proximal portion of the elongate shaft 108 to the distal portion of the elongate shaft 108, such as up to or beyond the proximal end of the balloon 110. A portion of the elongate shaft 108 can include an additional guidewire lumen 118. The guidewire lumen 118 can extend at least under the balloon 110, such as between a distal guidewire lumen port 120 and a proximal guidewire lumen port 122. The proximal guidewire lumen port 122 can be located somewhat proximal to the balloon 110, such as in a mid-portion of the elongate shaft 108, in a rapid-exchange configuration. Alternatively, the guidewire lumen 118 can extend at least under the balloon 110, such as between a distal guidewire lumen port 120 and a proximal guidewire lumen port 122 that can be located all the way at a proximal end of the elongate shaft 108, in an OTW configuration.

In an illustrative example of such an elongate shaft 108 including a side-by-side affixed pair of hypotubes, an outer diameter of the elongate shaft 108 can be approximately 2 millimeters. For example, the outer diameter of the IVUS hypotube 106 can be approximately 1 millimeter, and the outer diameter of the adjacent inflation hypotube 104 can be approximately 1 millimeter.

The inflation hypotube 104 and the IVUS hypotube 106 can individually or collectively be made of a metallic material, a non-metallic material, or a combination of these. The materials used for the inflation hypotube 104 and the IVUS hypotube 106 can be different at different locations along the length of the elongate shaft, such as to help provide a desired rigidity characteristic, a desired flexibility characteristic, or a desired ultrasound transmission characteristic at a particular location of the elongate shaft 108 or to provide a desired overall characteristic of the intravascular stent delivery device 102.

For example, the balloon inflation hypotube 104 can be made a non-metallic polymer material, such as over its most distal 40 millimeters of length along the elongate shaft 108. The inflation hypotube 104 can be made of a metal or metallic material, such as over a portion of its length that is more proximal than the distal 40 millimeters. This combination can help to improve pushability in the more proximal portion of the elongate shaft and to improve flexibility in the more distal portion of the elongate shaft. The IVUS hypotube 106 can include a non-metallic polymer material along the entire length of the elongate shaft 108, or at least in one or more regions located at or near the balloon 110 at which IVUS imaging is to be performed using the IVUS transducer 126. This can help to transmit ultrasound through the IVUS hypotube 106 to and from the IVUS transducer 126 carried by and housed within the IVUS hypotube.

In an example, the IVUS transducer 126 can be adhesively or otherwise fixed within and to the IVUS hypotube 106, such as at a distal portion of the elongate shaft 108 at or near a proximal end of the balloon 110. Alternatively, the IVUS transducer 126 can be removable from within the IVUS hypotube 106, such as by being part of a removable IVUS probe 124 extending through—and removable from—the IVUS lumen 116. In a removable IVUS probe 124 configuration, the IVUS probe 124 can be re-usable. Such re-usability may involve re-sterilization of the removable IVUS probe 124. A re-usable IVUS probe 124 configuration may offer cost-savings over multiple procedures, such as may be performed upon different patients.

In an illustrative embodiment of a monorail/rapid exchange configuration of the stent delivery device 102, the guidewire delivery lumen 118 can extend from (1) a distal guidewire port 120 at the distal tip of the stent delivery device 102 to (2) a proximal guidewire port 122 that provides a guidewire exit located at a mid-shaft portion of the stent delivery device 102, such as at about 25-30 centimeters proximal from the distal tip of the device 102. An illustrative approximate length of the stent delivery device 102 can be in the range from 130 centimeters to 150 centimeters, and the approximate outer diameter of the stent delivery device 102 is 4 French or less. An approximate length of the stent 112 is in the range from 4 millimeters to 31 millimeters. The approximate unexpanded stent profile (outer diameter) is in the range from 1 millimeter to 1.5 millimeters. The approximate distal tip profile of the device 102 is about 0.5 millimeters.

Figure 1C:
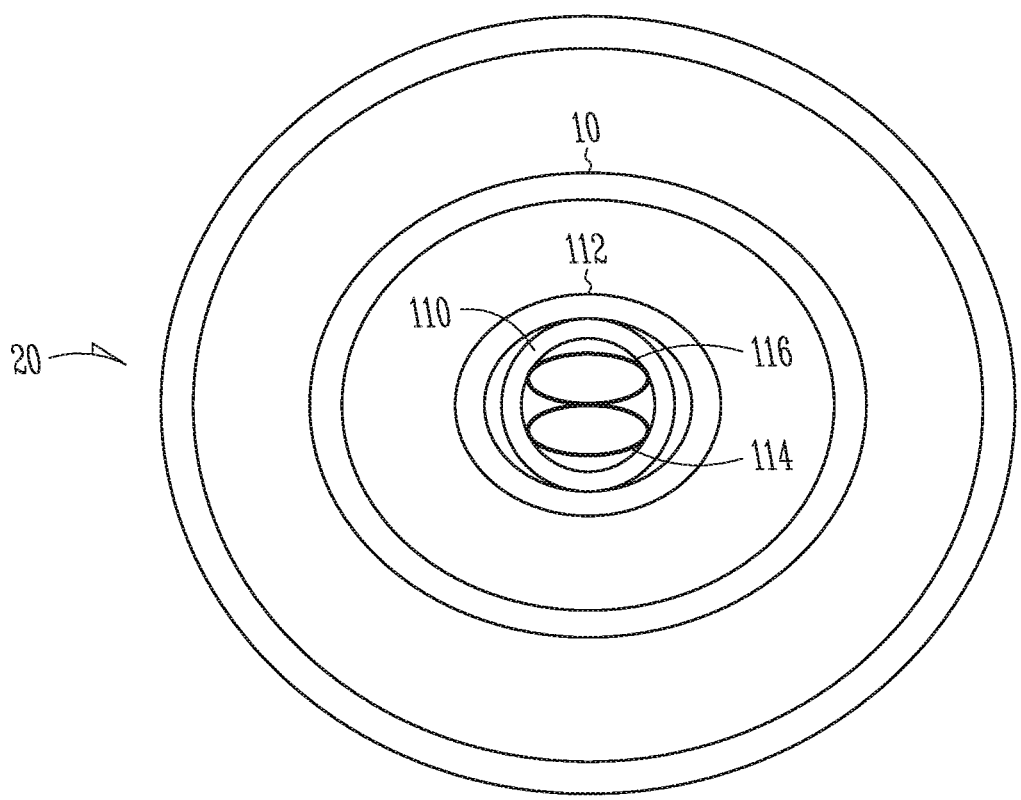
FIG. 1C shows a schematic illustration of a cross-sectional view taken along the cutline 1C-1C in FIG. 1B.
Figure 1D:
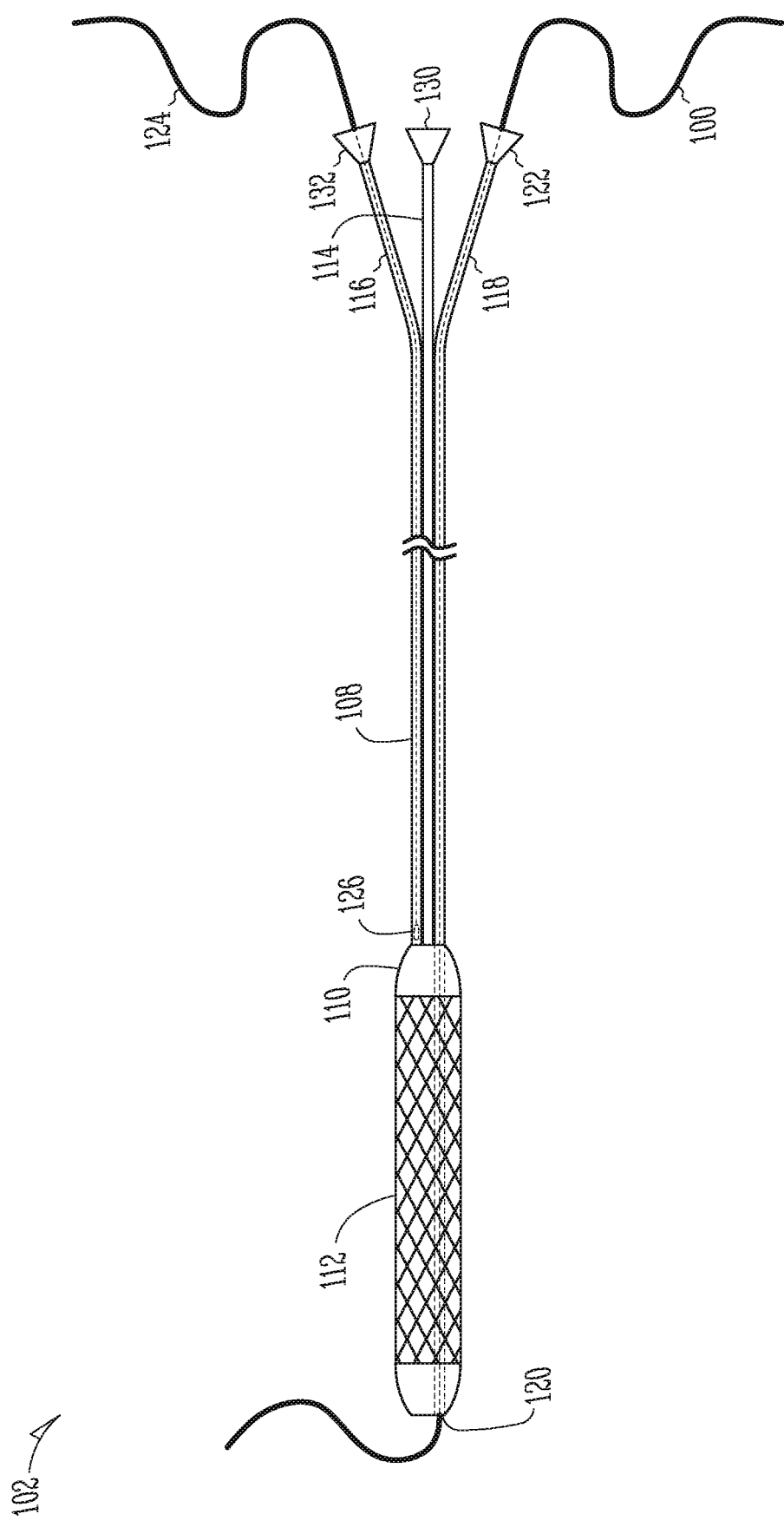
FIG. 1D is a schematic illustration showing a side view of portions of an embodiment of a guided stent delivery system that can include a stent delivery device, similar to that illustrated in FIG. 1B, but with FIG. 1D showing an Over-The-Wire (OTW) configuration in which a proximal guidewire exit port is located at a proximal end of the stent delivery device.

FIG. 1C shows a schematic illustration of a cross-sectional view taken along the cutline 1C-1C in FIG. 1B. FIG. 1C depicts a cross section of the coronary artery 10. The section of the stent delivery device 102 is represented in FIG. 1C by showing the section of the inflation hypotube 104 providing the inflation lumen 114, the section of the IVUS hypotube 106 providing the IVUS lumen 116, and the section of the unexpanded stent 112 being carried upon the section of the balloon 110.

Figure 2A:
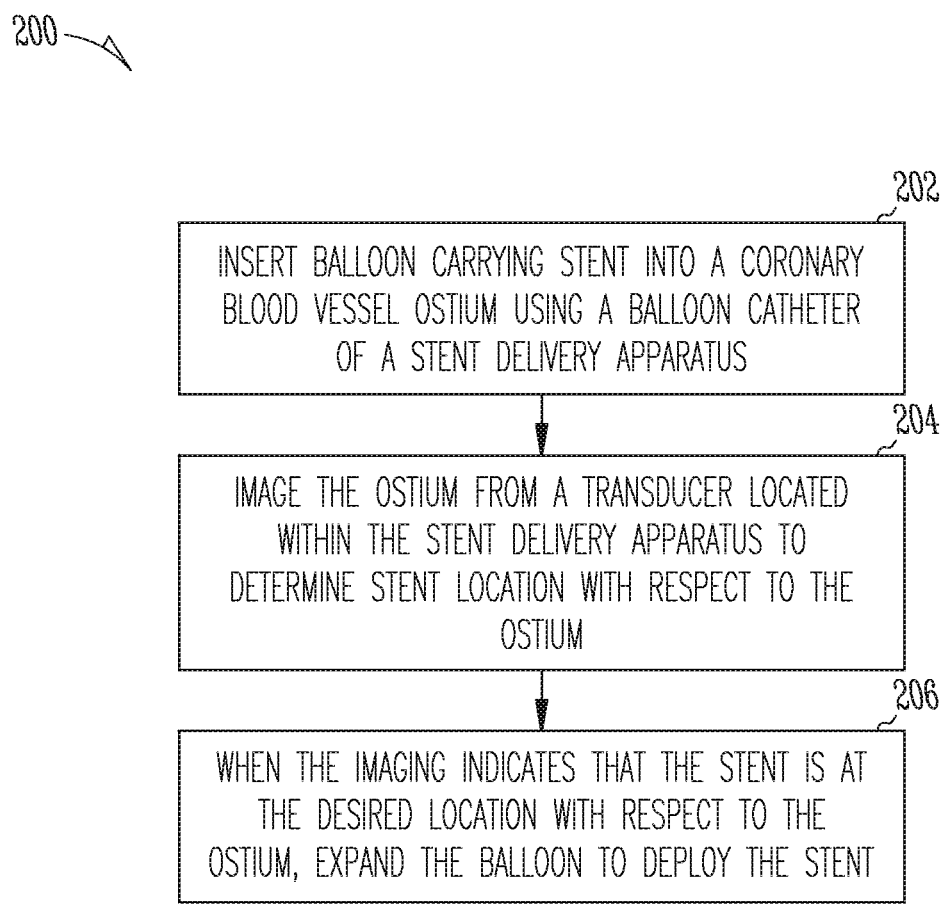
FIG. 2A is a flow chart showing an example of portions of a method of using onboard imaging of a stent delivery device to determine proper placement of a stent, before expanding and deploying the stent at the desired location using a balloon of a balloon catheter provided by the stent delivery device.

FIG. 2A is a flow chart showing an example of portions of a method 200 of using onboard imaging of a stent delivery device 102 to determine proper placement of a stent 112—including before expanding and deploying the stent 112 at the desired ostium location using a balloon 110 of a balloon catheter provided by the stent delivery device 102. Although this portion of the description may focus on a specific example of stenting a coronary blood vessel ostium, a similar approach can be taken to stent an ostium elsewhere in the vasculature, such as a renal artery ostium, a mesenteric artery ostium, or the like.

Before performing the acts shown in FIG. 2A, some preliminary steps are taken. An intravascular guidewire 100 can be inserted into a patient's vasculature, such as at a wrist (e.g., radial artery) or femoral vascular access point of the patient. The guidewire 100 can be fluoroscopically guided through the patient's vasculature to the patient's heart and into a coronary vessel presenting an ostial lesion to be stented, such as via the ostium of that coronary vessel, such as shown in FIG. 1A.

More particularly, in a coronary ostium stenting example, first, access to the vasculature can be obtained at a radial or femoral artery access point. A 10 cm sheath can be introduced at the access point. The sheath can include one or more valved ports through which one or more other instruments can then be inserted. Next, an atraumatic J-tip wire (e.g., 0.035 inch diameter) can be introduced via the port in the sheath and advanced through the vasculature, such as up to the aortic valve, as can be observed fluoroscopically. Then, using a "co-pilot" two-port extension manifold inserted into the sheath, a JR4 guide catheter (e.g., with a 2 mm inner diameter lumen) can be inserted over the J-tip guidewire until its distal end reaches the mouth of the coronary artery 10. A distal end of the JR4 guide catheter can be manipulated into the mouth of the coronary artery 10, i.e., the coronary ostium 20, such as shown in FIG. 3. The J-tip wire can then be removed. A contrast-agent enhanced fluid can be introduced via the JR4 guide catheter and observed angiographically to confirm that the distal end of the JR4 guide catheter has been properly introduced into the coronary ostium 20. The thinner (0.014 inch) intravascular guidewire 100 can then be introduced into the coronary artery via the JR4 guide catheter.

At 202 of FIG. 2A, after this thinner guidewire 100 is in place, within the JR4 guide catheter, the stent delivery device 102, with its distal portion including its balloon 110 carrying a stent 112, can be inserted along the pathway of the guidewire 100. The guidewire 100 is threaded through a guidewire delivery lumen 118 of the stent delivery device 102, to introduce and pass the distal portion of the stent delivery device 102 along the guidewire 100. This can include using either an over-the-wire (OTW) technique or a monorail/rapid exchange technique. The monorail/rapid exchange technique employs a shorter guidewire delivery lumen 118 or constraint than an OTW technique, as explained above. The introduction of the stent delivery device 102 can be observed fluoroscopically, if desired. However, as explained herein, neither fluoroscopy nor angiography will necessarily provide sufficiently detailed imaging information to allow the physician to determine proper placement of the stent 112, such as with a proximal end of the stent properly aligned with a plane defined by the ostium opening into the aorta.

At 204, after placing the distal portion of the stent delivery device 102 located within the vasculature such that the stent 112 is approximately at its desired placement and deployment location with respect to the ostial lesion to be stented, the ostium 20 can be imaged by the IVUS transducer 126 that is located onboard the distal portion of the stent delivery device 102. Such 360 degree circumferential imaging information from the IVUS imaging transducer 126 can be communicated to an external signal processor and displayed on a display screen. The displayed IVUS imaging information can help the user determine the location of the stent 112 with respect to the ostium. With such onboard IVUS imaging information available to the user at the time of stent placement, the user can slightly further insert or retract the stent delivery device 102 along the guidewire 100 until a proximal edge of the stent 112 is aligned with the plane defined by the ostial opening of the ostium 20.

With the imaging transducer 126 located onboard the stent delivery device 102 just proximal to the balloon 110 carrying the stent 112, good 360 degree circumferential information can be obtained for visualizing the plane defined by the ostial opening of the ostium 20, for visualizing a proximal edge of the stent 112, and for visualizing alignment between the two, as desired for proper ostial stent placement.

At 206, when the IVUS imaging indicates that the stent 112 is at this desired location with respect to the ostium 20 (e.g., proximal edge of the stent aligned with the plane defined by the ostial opening of the ostium 20) then the user can expand the balloon 110 to expand and deploy the stent 112 at the desired location with respect to the ostium 20. Using this approach, proper stent placement can be determined using onboard imaging, without having to withdraw the stent delivery device 102 to insert a separate IVUS probe along the guidewire 100 to perform imaging, followed by re-insertion of the stent delivery device 102 to use any imaging information provided by the separate IVUS probe.

In practice, at 204 and 206, the specified offset distance spacing between the proximal edge of the stent 112 and the IVUS transducer 126 can be used together with a pullback technique to place the stent 112 with its proximal edge aligned with the plane defined by the ostium 20 opening into the aorta. More particularly, the distal portion of the stent delivery device 102 can be inserted to position the stent 112 within the coronary blood vessel 10 with the IVUS transducer 126 located slightly distal to the plane defined by the ostium 20 opening into the aorta. Then, the pullback motor/actuator of the IVUS interface componentry 128 can provide mechanized pullback while the IVUS transducer 126 performs circumferential imaging. The IVUS images created during pullback can be stitched together to form a cylindrical image. When these image indicate that the IVUS transducer 126 is aligned with the plane defined by the ostium 20 opening into the aorta, the user can command the pullback motor/actuator of the IVUS interface componentry 128 to further pull back the stent delivery device 102 by an amount of the specified offset distance spacing between the proximal edge of the stent 112 and the IVUS transducer. Doing so will position the proximal edge of the stent 112 aligned with the plane defined by the ostium 20 opening into the aorta.

Further, an even longer pullback can similarly be used pre-deployment to verify that the entire lesion will be supported by the stent 112. More particularly, it is desired that the stent 112 be placed such that it spans the ostial lesion to be treated, otherwise dissection of atherosclerotic tissue at the distal edge of the stent 112 can occur, which can reduce the efficacy of the stenting procedure and can lead to complications. By inserting the stent delivery apparatus 102 such that the IVUS transducer 126 is located more distal to a distal edge of the lesion, and creating a stitched-together cylindrical IVUS image by mechanized pullback from such initial insertion location until the IVUS transducer 126 is located in alignment with the plane defined by the ostium 20 opening into the aorta, the distance that will be spanned by the stent 112 to be deployed can be verified, pre-deployment, since the offset distance from the IVUS transducer 126 to each of the proximal and distal edges of the stent 112 is known. The IVUS images created during pre-deployment pullback can therefore include both images at or near a distal edge of the stent 112 and images at or near a proximal edge of the stent 112, such that proper placement of both edges of the stent 112 can be assessed, pre-deployment, without requiring removal of the stent delivery apparatus 102.

FIG. 2B is a flow chart showing an example of portions of a method 208 of using onboard imaging of a stent delivery device 102 to confirm proper placement of the stent 112, after expanding and deploying the stent 112 at the desired location using the balloon 110 of the balloon catheter provided by the stent delivery device 102.

At 210, after expanding the balloon 110 to expand and deploy the stent 112, the balloon 110 can be deflated.

At 212, after deflating the balloon 110, the stent delivery apparatus 102 can be slightly further advanced into the coronary vessel beyond its ostium 20. This will locate the onboard IVUS transducer 126 (which is just proximal to the balloon 110) into coaxial interior alignment with a proximal edge of the stent 112.

At 214, after such slightly further advancement of the distal portion of the stent delivery apparatus 102, further IVUS imaging using the onboard IVUS transducer 126 can be performed. Such imaging can confirm that the edge of the stent 112 is properly aligned with the plane of the ostial opening of the ostium 20, without the proximal edge of the stent 112 being located too deep within the coronary vessel to provide desired stenting of the ostial lesion at the ostium 20, and without the proximal edge of the stent 112 protruding out beyond the ostium 20 into the vasculature.

In practice, at 212 and 214, it may be desired, after deflating the balloon 110, to advance the stent delivery apparatus 102 further into the coronary vessel such that the IVUS transducer 126 is located even more distal than a distal edge of the stent 112, and the mechanized pullback provided by the IVUS interface componentry 128 can be used to create stitched-together cylindrical image of the coronary vessel distal to the stent 112, including at the distal boundary of the stent 112. It is desired that the stent 112 be placed such that it spans the ostial lesion to be treated, otherwise dissection of atherosclerotic tissue at the distal edge of the stent 112 can occur, which can reduce the efficacy of the stenting procedure and can lead to complications. In sum, confirmation of proper placement of the stent 112 can include using the IVUS imaging not only to verify proper placement of the proximal edge of the stent 112, but also, to verify proper placement of the distal edge of the stent 112. The IVUS images created during pullback can therefore include both images at or near a distal edge of the stent 112 and images at or near a proximal edge of the stent 112, which can be obtained during the same or different pullbacks, and which need not require removal of the stent delivery apparatus to perform such imaging confirmation.

In FIGS. 2A, 2B, the onboard IVUS imaging for pre-placement stent location determination and for post-placement stent placement and deployment confirmation can each be performed (1) using an onboard IVUS transducer 112 that is fixed with respect to the balloon 110; or (2) using an onboard IVUS transducer 112 that is on a removable probe that can be inserted via the IVUS hypotube 106 into a desired position with respect to the balloon 110 and then removed via the IVUS hypotube 106—without requiring removal of the stent delivery device 102 from the guidewire 110 because of the IVUS hypotube 106 is fixed to the balloon inflation hypotube 104 along the shared elongate shaft 108. In this way, the IVUS hypotube 106 can provide an IVUS lumen, such as the IVUS lumen 116, with allows a fixed IVUS transducer 126 to be connected via a signal communication conduit, such as an electrical or optical signal conductor, to external signal processing componentry. Similarly, the IVUS hypotube 106 can provide an IVUS lumen, such as the IVUS lumen 116, which allows a removable IVUS transducer 126 located on a probe inserted into the IVUS lumen 116 to be retracted therefrom after imaging, such as for re-sterilization and re-use in a subsequent procedure, if desired.

Figure 2C:
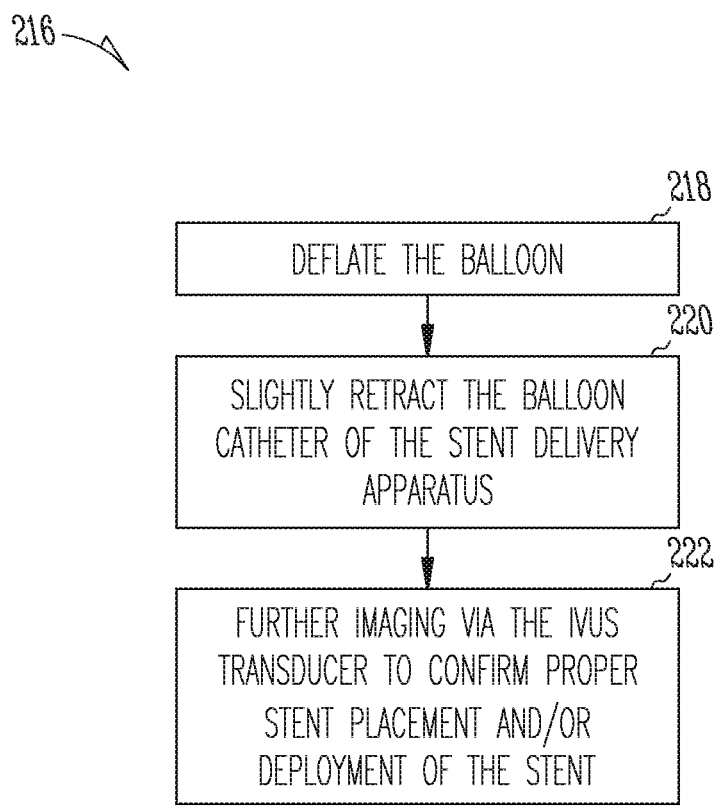
FIG. 2C is a flow chart illustrating portions of a method, similar to the method in FIG. 2B, but in which instead of further inserting the balloon catheter of the stent delivery apparatus, after deflating the balloon, in FIG. 2C, the balloon catheter of the stent delivery apparatus is slightly retracted for performing the IVUS imaging for confirming stent placement.

FIG. 2C is a flow chart illustrating portions of a method 216, similar to the method 208 in FIG. 2B, but in which instead of further inserting the balloon catheter of the stent delivery apparatus 102 at 212, after deflating the balloon at 210, in FIG. 2C, at 220, the balloon catheter of the stent delivery apparatus 102 is slightly retracted for performing the IVUS imaging for confirming stent placement. This may be useful, for example, if the stent was introduced and placed too far into the coronary blood vessel, such that a slight retraction of the stent delivery apparatus 102 is helpful to align the 360 degree circumferential imaging of the IVUS transducer 126 with the plane of the ostial opening of the ostium 20 to view and analyze stent placement and/or deployment.

FIG. 3 shows a schematic illustration of the stent delivery device 102 with the balloon 110 carrying the unexpanded stent 112 at an ostial lesion 300, with the guide catheter 304 routing the stent delivery device 102 back through the vasculature of the aorta 302.

FIG. 4 is similar to FIG. 3, but with the stent 112 having been expanded by the balloon 110.

User-Attachable-Detachable IVUS Hypotube or Other Imaging Catheter

FIG. 5 shows an example of portions of the stent delivery device 102 of FIG. 1B. In FIG. 5, however, the elongate shaft 108 can include an interventional device, such as a first hypotube or other similar tubular inflation tube 104 structure defining an inflation lumen 114 that is one or both of end-user-attachable and/or end-user-detachable from an imaging catheter, such as the second hypotube or other similar tubular IVUS tube 106 structure defining an IVUS lumen 116 (and vice-versa). Thus, as depicted in FIG. 5, the interventional device, such as the inflation tube 104, and the imaging catheter, such as the IVUS tube 106, need not be permanently affixed to each other at manufacture. Instead, the interventional device, such as the inflation tube 104, and the imaging catheter, such as the IVUS tube 106, can be provided at manufacture in a manner (1) that permits a physician, nurse, or other end-user to attach the inflation tube 104 or other interventional device to the IVUS tube 106 or other imaging catheter, or (2) that permits the end-user to detach the inflation lumen 104 or other interventional device from the IVUS tube 106 or other imaging catheter, or both (1) and (2). This can be advantageous, for example, where it is desirable to use the IVUS tube 106 or other imaging catheter with a variety of one or more different interventional devices, such as the inflation tubes 104, such as which are compatible for end-user attachment/detachment from the IVUS tube 106 or other imaging catheter. For example, this can permit the end-user to selectively attach or detach the IVUS tube 106 or other imaging catheter to an interventional device, such as to an inflation tube 104 of a desired first stent-delivery device 102 that is configured as an OTW device, or to selectively attach or detach the IVUS tube 106 to an interventional device such as to an inflation tube 104 of a desired second stent-delivery device 102 that is configured as an rapid-exchange device, depending on which type of such interventional device is most suitable for the procedure that the end-user wants to perform. The selection of which particular inflation tube 104 (or other interventional device) or IVUS tube 106 (or other imaging catheter) is to be end-user attached or end-user-detached from the other can depend on which particular devices are most appropriate for a particular procedure, and different options can be provided together in a kit or otherwise, or separately provided. The end-user-attachment, end-user-detachment, or both, can be performed quickly and conveniently and, as shown in the example of FIG. 5, need not require that the end-user use any special separate tool or fixture to perform the end-user-attachment and/or and-user-detachment.

FIG. 5 shows an example of portions of the interventional device, such as the stent delivery device 102, that can include one or more couplers 502. The one or more couplers 502 can be located at corresponding locations along the elongate shaft 108. An individual coupler 502 can be located on the inflation tube 104 or other interventional device or it can be located on the IVUS tube 106 or other imaging catheter. For a particular individual coupler 502 on one of the IVUS tube 106 or other imaging catheter or the inflation tube 104 or other interventional device, a corresponding mating, complementary, or other corresponding coupler 502 can be similarly located on the other of the inflation tube 104 or other interventional device or the IVUS tube 106 or other imaging catheter, such as to permit quick, convenient, and optionally toolless end-user attachment and/or detachment therebetween. For example, a spacing between adjacent couplers 502 on the IVUS tube 106 or other imaging catheter can correspond to a spacing between corresponding adjacent couplers 502 on the inflation tube 104 or other interventional device.

In FIG. 5, one or more of the couplers 502 on one of the IVUS tube 106 or other imaging catheter or the inflation tube 104 or other interventional device can include protrusions (sometimes referred to as "male" features) that can be engaged by one or more complementary receptacles (sometimes referred to as "female" features) on the other one of the inflation tube 104 or other interventional or the IVUS tube 106 or other imaging catheter, which can be appropriately spaced along the length of the elongate shaft 108, such as described above. Such opposing couplers 502 can also be magnetized with opposite polarity, such as to attract the opposing couplers 502 toward each other. This can help guide the opposing complementary couplers 502 toward each other to assist or ease end-user attachment of inflation tube 104 or other interventional device to the IVUS tube 106 or other imaging catheter. Such magnetization can also help hold the inflation tube 104 or other interventional device in attachment with the IVUS tube 106 or other imaging catheter during use of the stent delivery device 102 or other interventional device. Optionally, one of the opposing couplers 502 can be magnetized, with the other opposing coupler 502 being ferrous or oppositely magnetized or otherwise capable of being attracted by a permanent or other magnet.

Additionally or alternatively, the opposing complementary couplers 502 can include one or more snap-on or snap-in features that can allow end-user attachment by snapping opposing couplers 502 to each other at one or more locations along the length of the elongate shaft 108 of either of the imaging catheter or the interventional device. In such a case, it may be desirable to configure such snap-on or snap-in features with a release feature that permits the end-user to decouple and detach such opposing couplers 502 from each other, such as to detach the IVUS tube 106 or other imaging catheter from the inflation tube 104 or other interventional device.

In another example, the couplers 502 on one of the IVUS tube 106 or other imaging catheter or the inflation tube 104 or other interventional device need not include opposing complementary couplers 502 on the other of the IVUS tube 106 or other imaging device or the inflation tube 104 or other interventional device. For example, the one or more couplers 502 on one of the IVUS tube 106 or other imaging catheter or the inflation tube 104 or other interventional device can include a loop or collar or sleeve that is sized and shaped to permit an opposing one of the inflation tube 104 or other interventional device or the IVUS tube 106 or other imaging catheter to be slid into engagement, such as by a physician or other end-user. This slidable engagement can include positioning a distal end of one of the inflation tube 104 or other interventional device or the IVUS tube 106 or other imaging catheter near a coupler 502 that is located at or near a proximal end of the other of the inflation tube 104 or other interventional device or the IVUS tube 106 or other imaging catheter. That other component can be then inserted axially through the most proximal coupler and through any more distal couplers, such as until it abuts an appropriately-spaced stop that can be provided on the opposing one of the inflation tube 104 or other interventional device or the IVUS tube 106 or other imaging catheter. In such a manner, these components can be brought into a desired axial alignment with each other. Such axial end-user attachment and/or detachment of the inflation tube 104 or other interventional device with the IVUS tube 106 or other imaging catheter can additionally or alternatively include a longitudinal rail or track on one of the inflation tube 104 or other interventional device or the IVUS tube 106 or other imaging catheter, with a corresponding complementary one of a rail or track on the other one of the inflation tube 104 or other interventional device or the IVUS tube 106 or other imaging catheter, also with an optional appropriately located stop.

In an example in which one of the inflation tube 104 or other interventional device or the IVUS tube 106 or other imaging catheter is longitudinally slid into and out of engagement with the other of the inflation tube 104 or other interventional device or the IVUS tube 106 or other imaging catheter, the IVUS transducer 126 or other imaging transducer carried by the IVUS tube 106 or other imaging catheter can optionally be permanently affixed at a specified location at or near a distal end of the IVUS tube 106 or other imaging catheter. In such an approach, the sliding action of the IVUS tube 106 or other imaging catheter with respect to the inflation tube 104 or other interventional device can optionally be used for longitudinal positioning of the IVUS transducer 126 or other imaging transducer at a desired longitudinal location with respect to the inflation tube 104 (or other interventional device) or a portion thereof.

FIGS. 6A, 6B, 6C, and 6D show an example of an end-user-attachable and end-user-detachable IVUS, OCT, or other imaging catheter 600 that can be used as a standalone imaging catheter 600 for performing imaging (with or without a stent-delivery catheter or other interventional device 602). In this example, the imaging catheter 600 can optionally be end-user-attached and end-user-detached from a separate interventional device 602—without requiring that the interventional device 602 include any special mating or other attachment features, such as the couplers 502 of FIG. 5. Thus, the approach described with respect to FIGS. 6A, 6B, 6C, and 6D can be flexible enough to permit the imaging catheter 600 to be used with a wide variety of stent-delivery catheter devices or other interventional devices 602. Such interventional devices 602 need not be specially adapted for use with the end-user-attachable and end-user-detachable imaging catheter 600.

Figure 6A:
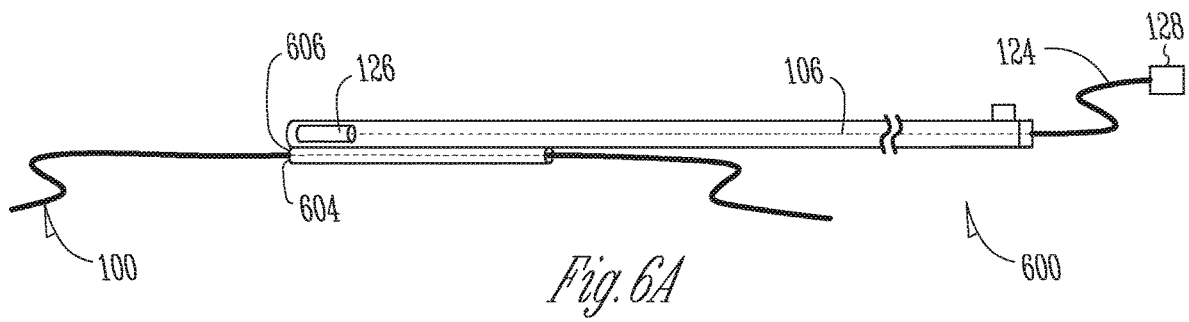
FIGS. 6A, 6B, 6C, and 6D illustrate an example in which an IVUS device can be standalone or attachable to another instrument, such as a stent-delivery catheter, without requiring that the other instrument have any special attachment features.

FIG. 6A shows an example of an imaging catheter 600. The imaging catheter 600 can include an imaging transducer tube, similar to the IVUS tube 106 described above. The imaging transducer tube can house an IVUS, OCT, or other imaging transducer 126, an IVUS probe 124 or other imaging probe, and external interface componentry 128, such as explained above. However, in the example of FIGS. 6A, 6B, 6C, and 6D, the IVUS tube 106 or other imaging transducer tube need not be attached at manufacture to an interventional device, such as the inflation tube 104. Instead, the imaging catheter 600 can serve as either a standalone imaging catheter 600 or as an imaging catheterization 600 that can be couplable or attachable to a stent-delivery catheter 602 or other interventional instrument or device. For example, the imaging catheter 600 can include an elongate IVUS tube 106 or other imaging transducer tube, along a portion of which at least one elongate deformable or elastic sleeve 604 can be attached. For example, an outer surface of the elastic sleeve 604 can be attached to an outer surface of the elongate body of the imaging catheter 600, such as shown in FIGS. 6A, 6B, 6C, and 6D, such as by welding using heat or ultrasound, using adhesive, such as cyanoacrylate, or using a combination of both techniques.

The elastic sleeve 604 can define an inner lumen 606, such as can extend the entire length of the elastic sleeve 606 and opening at each end of the elastic sleeve 606. The inner lumen 606 of the elastic sleeve 604 can serve as a rapid exchange port for a guidewire or other instrument or interventional device, such as explained herein. More particularly, the inner lumen 606 of the elastic sleeve 604 can have an inner diameter that is sized and shaped to accommodate insertion of a desired interventional instrument or device therethrough. The elasticity of the elastic sleeve 604 can allow the inner diameter of the inner lumen 606 to stretch and expand, such as to accommodate passage (and optional gripping, stabilization, and securing) of an interventional device or other instrument therethrough having an outer diameter that is larger than the "resting" (non-stretched) inner diameter of the inner lumen 606. The inner lumen 606 of the elastic sleeve 600 can optionally include an appropriate hydrophilic coating to help make the inner wall of the inner lumen 606 of the elastic sleeve 600 slippery enough to accommodate insertion of an interventional device 610 therethrough. The hydrophilic coating can be selected to provide a desired amount of friction between the elastic sleeve 600 and the inserted interventional device 610 so as provide enough of an "interference fit" to hold or stabilize the interventional device 610 in place within the inner lumen 606 of the elastic sleeve 600.

For example, a standard guidewire 100 can have an outer diameter of approximately 0.35 millimeters. In this example, the inner diameter of the inner lumen 606 can be sized to be approximately 0.5 millimeters without stretching. Such an arrangement can permit the guidewire 100 to be easily inserted into the inner lumen 606 of the elastic sleeve 604 and easily passed therethrough without being "gripped" by stretching of the inner lumen 606 of the elastic sleeve 604. The length of the elastic sleeve 604 can be long enough so that it can stabilize or secure an interventional device or other instrument inserted therethrough that expands the inner diameter of the elastic sleeve 604. In an illustrative example, the elastic sleeve 604 can be between 0.3 cm and 50 cm in length, such as between 2 cm and 5 cm in length, in an example, or about 25 cm in length, in another example. Multiple elastic sleeves 604 (or axially-shorter loops) can optionally be provided, such as at desired locations along a length of the IVUS device 600. The elastic sleeve 604 can include a material suitable for stretching and gripping, such as silicone, polyurethane, PEBAX® elastomer that can include rigid polyamide blocks and soft polyether blocks, or another suitable material.

Figure 6B:
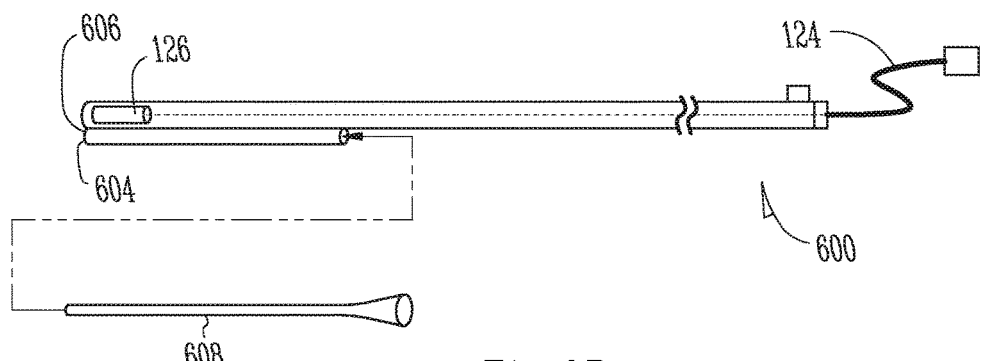

FIG. 6B is similar to FIG. 6A, but includes an introducer sheath 608 that can be sized and shaped to be inserted into the inner lumen 606 of the elastic sleeve 604, such as to extend within the entire length of the inner lumen 606 of the elastic sleeve 604, such as leaving an outwardly-flared or other proximal end protruding out from the proximal opening of the inner lumen 606 of the elastic sleeve 604. The outward flaring can provide a region of larger inner diameter at the proximal end of the introducer sheath 608, such as to permit an instrument to be more easily inserted therein. The introducer sheath 608 can have an outer diameter that is larger than the "resting" inner diameter of the inner lumen 606 of the elastic sleeve. In this way, the introducer sheath 608 can be used to pre-stretch the inner lumen 606 of the elastic sleeve 604, so that an instrument can be easily inserted and freely slid through an inner lumen of the introducer sheath 608. The introducer sheath 608 can be a "peel-away" introducer sheath 608, which can be scored longitudinally on opposing sides of the peel-away introducer sheath 608, such as to create indentations or weakened regions. This can help permit a user to separate the introducer sheath 608 into two pieces by pulling apart on two opposing sides of the introducer sheath 608. This allows easy peeling-away separation of the introducer sheath 608 into two pieces that can be pulled proximately by the user and thereby removed from the inner lumen 606 of the elastic sleeve 604. After freely and easily inserting and sliding a stent-delivery catheter or other desired instrument through the introducer sheath 608 to a desired longitudinal position with respect to the introducer sheath 608, the end-user can peel part the introducer sheath 608, thereby permitting the inner lumen 606 of the elastic sleeve 604 to grip and secure the interventional device or other instrument passed therethrough.

FIG. 6B shows an example of the introducer sheath 608 laid next to the elastic sleeve 604 of the imaging catheter 600.

Figure 6C:
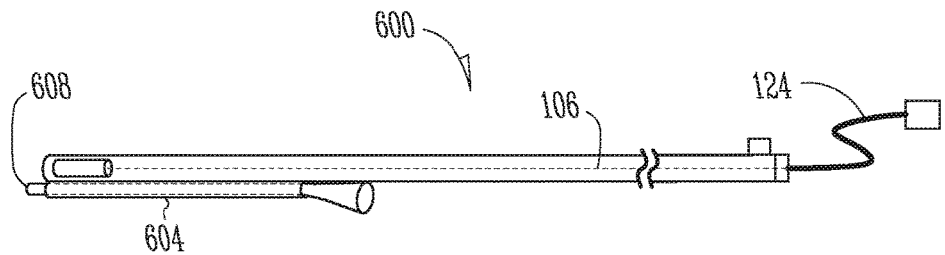

FIG. 6C shows an example of the introducer sheath 608 introduced within the inner lumen 606 of the elastic sleeve 604 of the imaging catheter 600, but before the introducer sheath 608 has been peeled-apart and removed therefrom.

Figure 6D:
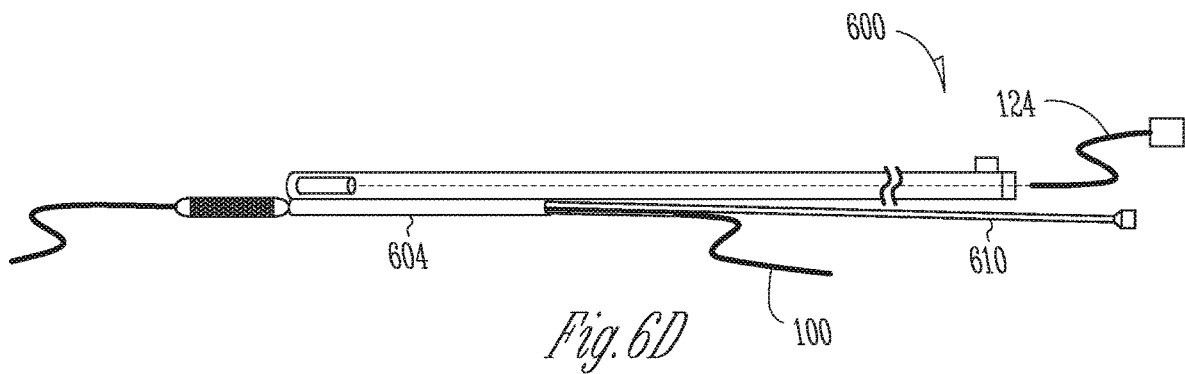

FIG. 6D shows an example after a stent-delivery device or other interventional device 610 has been inserted through the introducer sheath 608, and after the introducer sheath 608 has been peeled apart and removed from the inner lumen 606 of the elastic sleeve 604, leaving the elastic sleeve 604 securely gripping the interventional device 610, after obtaining a desired longitudinal arrangement of the interventional device 610 with respect to the imaging catheter 600. For example, in FIG. 6D, the balloon and stent of the stent-delivery device or other interventional device 610 can be located just distal of the distal end of the imaging catheter 600, such that the IVUS transducer 126 or other imaging transducer within the IVUS tube 106 or other imaging tube of the imaging catheter 600 is located just proximal to a proximal end of the balloon on the stent-delivery device or other interventional device 610.

FIG. 7 shows another example, in which the elongate body of the imaging catheter 600 can be inserted through the elastic sleeve 604 and an outer surface of the elongate body of the imaging catheter 600 can be attached to an inner surface of the elastic sleeve 604 such as by welding using heat or ultrasound, using adhesive, such as cyanoacrylate, or using a combination of both techniques. The elastic sleeve 604 can be sized large enough to be able to accommodate also inserting a guidewire, a stent-delivery catheter, or other interventional device through a passage 702 provided by the elastic sleeve 604. The elastic sleeve 604 can be stretchable. For example, the elastic sleeve 604 can be stretched such as by inserting an interventional device through a longitudinal passage in the elastic sleeve 604, which can then relax or shrink such as to grip or secure the interventional device to the imaging catheter 600 using the elastic sleeve 604. On the other hand, the elastic sleeve 604 can be sized so as to not be stretched by inserting a guidewire, which can be passed freely through the elastic sleeve 604. For example, an elastic sleeve 604 providing a tubular longitudinal inner lumen passage having an inner diameter of 0.4 millimeters, a guidewire having an outer diameter of 0.3 millimeters can be freely passed through the passage of the elastic sleeve. However, an interventional device 610 such as a stent delivery catheter can carry a stent having an outer diameter of 0.9 millimeters. In this example, the elastic sleeve 604 can be configured to accommodate passage of the 0.9 millimeter diameter stent, but the elastic sleeve 604 can then relax or shrink to grip and secure a 0.7 millimeter shaft of the stent delivery catheter, thereby attaching the imaging catheter 600 to the shaft of the stent delivery catheter or other interventional device 610.

In FIG. 7, a distal end of the elastic sleeve 604 can be spaced apart from a distal end of the imaging catheter 600 by an amount (e.g., between 1 to 2 millimeters, inclusive) that leaves the IVUS transducer 126 or other imaging transducer carried by the imaging catheter 600 exposed at a location that is more distal than the distal edge of the elastic sleeve 604. This can help avoid the elastic sleeve 604 interfering with imaging being performed by the IVUS transducer 126 or other imaging transducer.

FIG. 8 shows an example of the elastic sleeve 604 that can include an imaging window 802, such as through which imaging can be performed. For example, the imaging window 802 can be an opening or passage through which energy from the IVUS transducer 126 or other imaging transducer can pass more easily as compared to energy passing through portions of the elastic sleeve 604 other than the imaging window 802. In another example, the imaging window 802 need not constitute an opening or passage, but can instead constitute a "gel-pack" or other pouch carrying ultrasound impedance-matching gel or other substance through which ultrasonic imaging can be performed. Similarly, for another imaging modality, such as OCT, the imaging window 802 can be more transparent to optical energy from the OCT imaging transducer than other portions of the elastic sleeve 604. In an example in which the imaging window does not constitute an opening or passage, it can optionally span the entire distance from a proximal end of the elastic sleeve 604 to a distal end of the elastic sleeve 604. Also, in an example in which imaging can be performed through an open or other imaging window 802, a distal end of the elastic sleeve 604 can optionally be aligned with a distal end of the imaging catheter 600.

Figure 9:
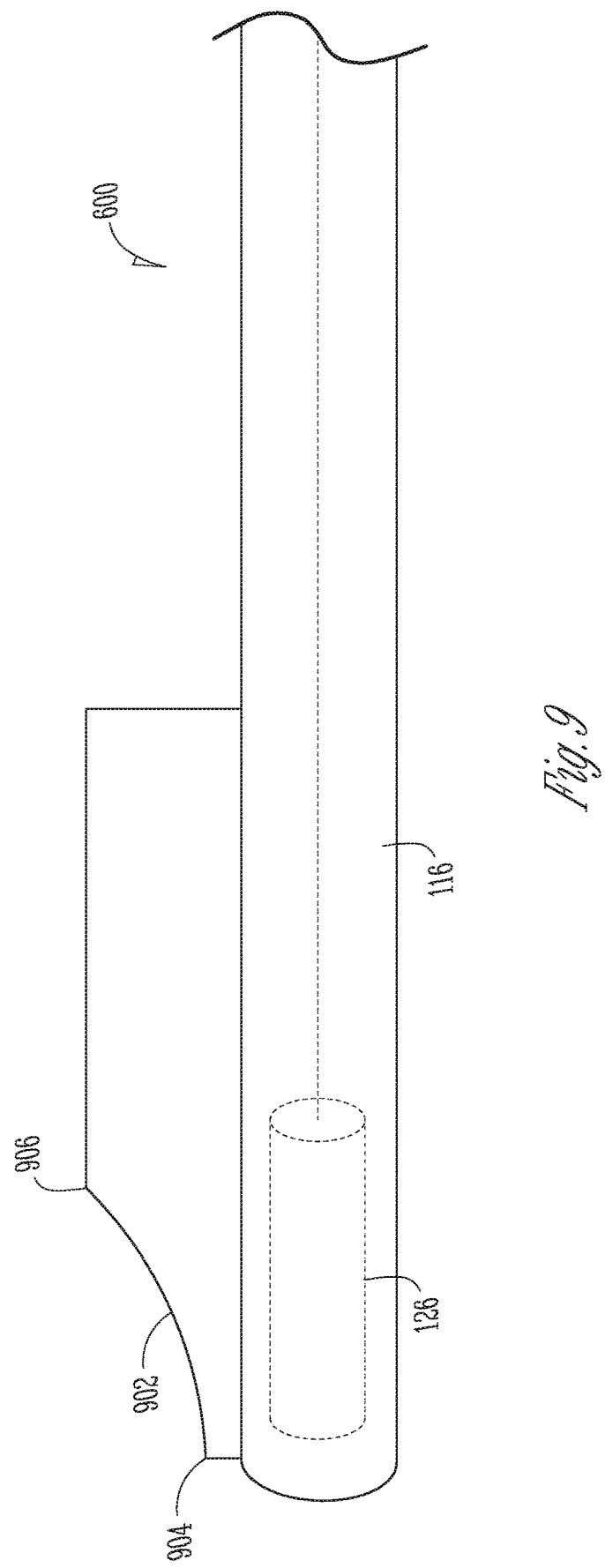
FIG. 9 illustrates a distal portion of the imaging catheter including a distal tapered edge of the elastic sleeve.

FIG. 9 illustrates a distal portion of the imaging catheter 600 including a distal tapered edge of the tubular elastic sleeve 604. In this example, the distal-most portion of the tubular sleeve 604 can include a cutout that defines a tapered end portion 902 of the sleeve 604. As shown in FIG. 9, at the tapered end 902 portion of the sleeve 604, the distal-most leading edge 904 portion of the tapered end portion 902 of the sleeve 604 can present a smaller cross-sectional lateral profile in a direction orthogonal to a central longitudinal axis of the imaging catheter 600. From the distal-most leading edge portion 904 of the tapered end portion 902 of the sleeve 604, the tapered end portion of the sleeve 604 can gradually broaden, e.g., linearly or in a curved manner as shown in FIG. 9, to the maximum cross-sectional lateral profile at the proximal edge 906 of the tapered end portion 902 of the sleeve 604. Such a tapered end portion 902 can help provide easier insertion of the imaging catheter 600, such as into a coronary artery or other blood vessel. It can permit the distal tip of the imaging catheter 600 to remain stable and to help avoid the distal tip of the catheter 600 and the laterally-projecting, lumen-providing sleeve 604 to not get caught up in plaque or side branches of a vessel into which the imaging catheter 600 is being introduced. This can help improve stability and minimize interference by the sleeve 604, such as during insertion or advancing of the imaging catheter 600 into the vessel. The tapered end portion 902 can also help provide a less obstructed lateral Field-Of-View of the IVUS, OCT, or other imaging transducer 126 that can be inserted via the lumen 116 toward the closed or open distal end of the imaging catheter 600.

In a similar manner to the tapered distal end portion 902 shown in FIG. 9, a similar proximal tapered end portion can be provided at a proximal end of the sleeve 604. This can help provide similar advantages to those already described with respect to the tapered distal end portion 902, such as during retraction or removal of the imaging catheter 600 from the vasculature.

Figure 10:
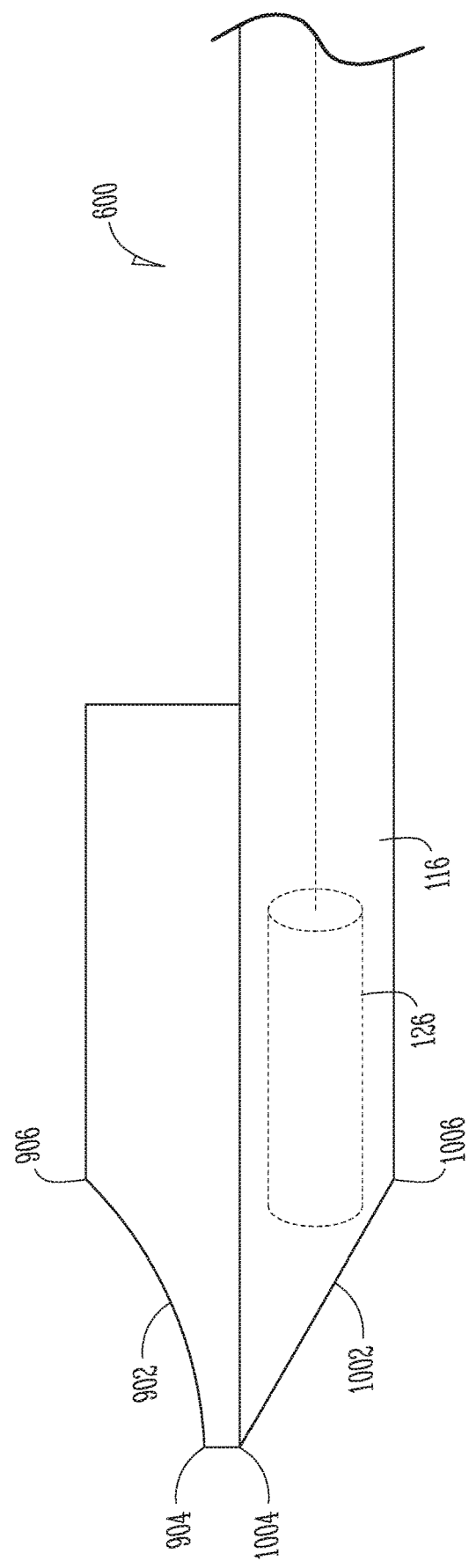
FIG. 10 is similar to FIG. 9, but FIG. 10 also shows the distal tip of the imaging catheter with a taper.

FIG. 10 is similar to FIG. 9, but FIG. 10 also shows, in addition to the tapering of the distal end portion 902 of the sleeve 604, the distal tip of the imaging catheter 600 can optionally also include a curved or straight taper 1002, such as can help ease insertion of the distal tip of the catheter 600 into a coronary artery or other blood vessel or other lumen of interest. As mentioned, the distal tip of the imaging catheter 600 can be closed, such that the imaging transducer 126 cannot extend out beyond the distal tip of the imaging catheter 600. The closed distal tip of the imaging catheter 600 need not be perpendicular to the central longitudinal axis defined by the imaging catheter 600, but can instead include a tapered distal end surface 1002, such as which can extend from a most-distal location 1004 to a more proximal location 1006. The tapered distal end surface 1002 can be oriented at an oblique angle to the central longitudinal axis defined by the imaging catheter 600. The tapered distal end surface 1002 can be similar to or different than the taper 902 shown in FIG. 9 with respect to the distal end portion 902 of the elastic sleeve 604. For example, the tapered distal end surface 1002 of the distal tip of the imaging catheter 600 can be oriented in an opposite direction from that of the tapered distal end portion 902 of the elastic sleeve 604, so as to create a low lateral profile by the combination of the sleeve 604 and the body of the imaging catheter 600. Alternatively, the tapered end surface 1002 of the distal tip of the imaging catheter 600 can extend in a consistent orientation to that shown with respect to the distal end portion 902 of the elastic sleeve 604.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method of using an imaging catheter apparatus, the method comprising:
   receiving an interventional medical device for coupling into alignment with an elongate shaft assembly of the imaging catheter apparatus, the elongate shaft assembly having a tube defining an internal tubular passage with a hermetically sealed distal end, the elongate shaft assembly is configured to carry an imaging transducer that is located and translatable within the tubular passage of the elongate shaft assembly of the imaging catheter apparatus;
   inserting an introducer sheath into an elastic sleeve to expand an inner diameter of a sleeve lumen of the elastic sleeve;
   inserting the interventional medical device into the introducer sheath inserted into the elastic sleeve; and
   peeling-away the introducer sheath to remove the introducer sheath from the elastic sleeve such that the interventional medical device remains within and gripped by the sleeve lumen of the elastic sleeve;
   moving at least one of the elongate shaft assembly or the imaging transducer located therewithin to image a target location for using the interventional medical device; and
   deploying the interventional medical device for performing a medical procedure at the target location using information obtained from an image of the target location obtained using the imaging transducer.

2. The method of claim 1, wherein the elastic sleeve is attached to an exterior of the tube of the elongate shaft assembly of the imaging catheter apparatus.

3. The method of claim 1, comprising freely passing a guidewire through the elastic sleeve without gripping the guidewire via the elastic sleeve.

4. The method of claim 1, comprising using the imaging catheter apparatus comprising:
   the elongate shaft assembly having a proximal shaft portion and a distal shaft portion, the elongate shaft assembly configured to carry the imaging transducer such that the imaging transducer is locatable at or near the distal shaft portion of the elongate shaft assembly; and
   at least one coupler, attached to the elongate shaft assembly, the at least one coupler configured to permit an end user to at least one of couple or attach at least one of a guidewire or the interventional medical device to the elongate shaft assembly via the at least one coupler.

5. The method of claim 4, wherein the coupling includes using the at least one coupler comprising the elastic sleeve that is included in or attached to the elongate shaft assembly.

6. The method of claim 5, wherein the coupling includes using the at least one coupler comprising the elastic sleeve that is included in or attached to the elongate shaft assembly, wherein the elastic sleeve is located at the distal shaft portion of the elongate shaft assembly.

7. The method of claim 5, comprising using the elastic sleeve, wherein the sleeve lumen extends longitudinally through the elastic sleeve, the inner diameter of the sleeve lumen is expandable and sized and shaped to grip around a portion of the interventional medical device to attach the imaging catheter apparatus thereto.

8. The method of claim 5, comprising using the elastic sleeve, wherein the sleeve lumen extends longitudinally through the elastic sleeve, the inner diameter of the sleeve lumen is sized and shaped to allow insertion and free passage of a 0.35 millimeter outer diameter guidewire therethrough.

9. The method of claim 5, comprising using the elastic sleeve, wherein the elastic sleeve defines a longitudinal sleeve lumen extending longitudinally through the elastic sleeve, the sleeve lumen including a "resting" inner diameter of about 0.5 millimeters, without stretching.

10. The method of claim 5, comprising using the elastic sleeve, wherein the elastic sleeve includes a length that is between 0.3 centimeters and 50 centimeters.

11. The method of claim 5, comprising using the elastic sleeve, wherein a distal end of the elastic sleeve is proximally offset from a distal end of elongate shaft assembly by at least 1 millimeter.

12. The method of claim 5, comprising using the elastic sleeve, wherein at least one of a distal end portion or a proximal end portion of the elastic sleeve is tapered to present a smaller cross-sectional profile than at a center region of the elastic sleeve.

13. The method of claim 5, comprising using the elastic sleeve, wherein an inner surface of the elastic sleeve includes a hydrophilic coating.

14. The method of claim 5, further comprising using the introducer sheath, sized and shaped to be inserted into the sleeve lumen of the elastic sleeve while stretching the inner diameter of the sleeve lumen to assist in advancing a wire or the interventional medical device into the elastic sleeve.

15. The method of claim 14, comprising using a balloon stent delivery A catheter or other interventional device that is sized and shaped to be inserted into the introducer sheath and to be held in place within the sleeve lumen of the elastic sleeve by a stretched inner diameter of the sleeve lumen.

16. The method of claim 5, comprising using the elastic sleeve, wherein the elastic sleeve includes an imaging window that more easily passes imaging energy than another portion of the elastic sleeve.

17. The method of claim 5, comprising using the elongate shaft assembly, wherein the elongate shaft assembly passes through, and is affixed to, the sleeve lumen of the elastic sleeve.

18. The method of claim 5, comprising using the elongate shaft assembly, wherein the elongate shaft assembly includes one of an intravascular ultrasound (IVUS) transducer, an optical coherence tomography (OCT) transducer, or other imaging modality transducer.

19. A method of using an imaging catheter apparatus, the method comprising:
   receiving an interventional medical device for coupling into alignment with an elongate shaft assembly of the imaging catheter apparatus, the elongate shaft assembly is configured to carry an imaging transducer;

inserting an introducer sheath into an elastic sleeve, attached to the elongate shaft assembly of the imaging catheter apparatus, to expand an inner diameter of a sleeve lumen of the elastic sleeve;

inserting the interventional medical device into the introducer sheath inserted into the elastic sleeve;

peeling-away the introducer sheath to remove the introducer sheath from the elastic sleeve such that the interventional medical device remains within and gripped by the sleeve lumen of the elastic sleeve;

moving at least one of the elongate shaft assembly or the imaging transducer located therewithin to image a target location for using the interventional medical device; and deploying the interventional medical device for performing a medical procedure at the target location using information obtained from an image of the target location obtained using the imaging transducer.

20. A method of using an imaging catheter apparatus, the method comprising:

receiving an interventional medical device for coupling into alignment with an elongate shaft assembly, of the imaging catheter apparatus, that is configured to carry an imaging transducer;

inserting the interventional medical device into an elastic sleeve, attached to the elongate shaft assembly of the imaging catheter apparatus, wherein the elastic sleeve expands to grip the interventional medical device;

moving at least one of the elongate shaft assembly or the imaging transducer located therewithin to image a target location for using the interventional medical device;

deploying the interventional medical device for performing a medical procedure at the target location using information obtained from an image of the target location obtained using the imaging transducer; and using the imaging transducer for imaging via an imaging window in the elastic sleeve.

\* \* \* \* \*

UNITED STATES PATENT AND TRADEMARK OFFICE
CERTIFICATE OF CORRECTION

PATENT NO. : 12,102,478 B2
APPLICATION NO. : 18/309183
DATED : October 1, 2024
INVENTOR(S) : Kahlon et al.

Page 1 of 1

It is certified that error appears in the above-identified patent and that said Letters Patent is hereby corrected as shown below:

On the Title Page

On page 2, in Column 2, item (56) under "Other Publications", Line 11, delete "Apr. 18, 2202" and insert --Apr. 18, 2022-- therefor In the Claims In Column 22, Line 47, in Claim 15, after "delivery", delete "A"

Signed and Sealed this
Nineteenth Day of November, 2024

Katherine Kelly Vidal
*Director of the United States Patent and Trademark Office*